US010161928B2

(12) United States Patent
Dahl et al.

(10) Patent No.: US 10,161,928 B2
(45) Date of Patent: Dec. 25, 2018

(54) WELLNESS PANEL

(75) Inventors: Andrew A. Dahl, Bloomfield Hills, MI (US); Denis M. Callewaert, Metamora, MI (US)

(73) Assignee: Wellmetris, LLC, Keego Harbor, MI (US)

( * ) Notice: Subject to any disclaimer, the term of this patent is extended or adjusted under 35 U.S.C. 154(b) by 0 days.

(21) Appl. No.: 13/812,220

(22) PCT Filed: Jul. 21, 2011

(86) PCT No.: PCT/US2011/044786
§ 371 (c)(1),
(2), (4) Date: Jan. 25, 2013

(87) PCT Pub. No.: WO2012/018535
PCT Pub. Date: Feb. 9, 2012

(65) Prior Publication Data
US 2013/0122518 A1    May 16, 2013

Related U.S. Application Data

(60) Provisional application No. 61/367,486, filed on Jul. 26, 2010.

(51) Int. Cl.
*G01N 33/50* (2006.01)
*G01N 33/68* (2006.01)
*G01N 33/53* (2006.01)

(52) U.S. Cl.
CPC .............. *G01N 33/50* (2013.01); *G01N 33/53* (2013.01); *G01N 33/6893* (2013.01); *G01N 2800/7009* (2013.01); *G01N 2800/7095* (2013.01); *Y10T 436/173076* (2015.01)

(58) Field of Classification Search
None
See application file for complete search history.

(56) References Cited

U.S. PATENT DOCUMENTS

| | | | |
|---|---|---|---|
| 4,303,409 A * | 12/1981 | Ogawa | G01N 33/82 422/420 |
| 6,372,514 B1 | 4/2002 | Lee | |
| 6,541,265 B2 | 4/2003 | Leeuwenburgh | |
| 6,753,159 B1 * | 6/2004 | Lee | C12Q 1/62 435/10 |
| 7,220,597 B2 | 5/2007 | Zin et al. | |
| 7,784,678 B2 * | 8/2010 | Kuo | G01N 35/00732 235/375 |
| 7,927,865 B2 | 4/2011 | Meathrel et al. | |
| 8,273,305 B2 | 9/2012 | Slowey et al. | |
| 2002/0001854 A1 * | 1/2002 | Lee | B01L 3/5023 436/518 |
| 2003/0109420 A1 * | 6/2003 | Valkirs | G01N 33/53 435/7.1 |
| 2005/0074745 A1 * | 4/2005 | Clayton | G01N 33/5038 435/4 |
| 2006/0222567 A1 | 10/2006 | Kloepfer et al. | |
| 2006/0281188 A1 * | 12/2006 | Mann | G01N 33/526 436/169 |
| 2007/0021929 A1 * | 1/2007 | Lemmo et al. | 702/22 |
| 2009/0012716 A1 * | 1/2009 | Urdea et al. | 702/19 |
| 2009/0215159 A1 | 8/2009 | Kirby | |
| 2010/0233746 A1 | 9/2010 | Sonntag et al. | |
| 2011/0137851 A1 | 6/2011 | Cavet et al. | |
| 2011/0312657 A1 | 12/2011 | Azimi et al. | |
| 2014/0072189 A1 | 3/2014 | Jena et al. | |

FOREIGN PATENT DOCUMENTS

| | | | |
|---|---|---|---|
| CA | 2597177 | 1/2012 | |
| EP | 1389445 | 2/2004 | |
| WO | WO 199848272 | 10/1998 | |
| WO | WO 2000028072 | 5/2000 | |
| WO | WO 2008001357 A2 * | 1/2008 | ....... G01N 33/57407 |
| WO | WO 2008140463 A2 * | 11/2008 | |
| WO | WO 2012047341 | 4/2012 | |
| WO | WO 2014042979 | 3/2014 | |
| WO | WO 2014113770 | 7/2014 | |

OTHER PUBLICATIONS

Delfino et al., Environmental Health Perspectives, 116(7), (2008), p. 899-906.*
Ispirlidis et al., Time-course of changes in inflammatory and performance responses following a soccer game, Clin. J. Sport Med., 18(5), (2008), p. 423-431.*
Apak et al., Total antioxidant capacity assay of human serum using copper(II)-neocuproine as chromgenic oxidant: The CUPRAC method, Free Radical Research, 39(9), (2005), p. 949-961.*
Scheet et al., Effect of Exercise on cytokines and Growth mediators in prepubertal children, Pediatric Research, 46, (1999), p. 429-434 (pdf document 13 pages).*
Storey, K., Functional Metabolism Regulation and Adaptation, (2004), ISBN: 978-0-471-41090-X, p. 350.*
Yim et al., Exercise-induced acute renal failure in a patient with congenital renal hypouricaemia, Nephrol Dial Transplant 13, (1998), p. 994-997.*

(Continued)

*Primary Examiner* — Ram R Shukla
*Assistant Examiner* — Ellen J Marcsisin
(74) *Attorney, Agent, or Firm* — Snell & Wilmer LLP

(57) ABSTRACT

A panel for monitoring levels of biomarkers, including an assay having at least one inflammation monitoring test, at least one oxidative stress monitoring test, and at least one antioxidant activity monitoring test. A method of monitoring an individual's health, by collecting a sample from the individual, applying the sample to an assay panel, performing at least one inflammation monitoring test, at least one oxidative stress monitoring test, and at least one antioxidant activity monitoring test in the panel, and determining levels of biomarkers related to inflammation, oxidative stress, and antioxidant activity and therefore providing information regarding the individual's relative health and/or risk of developing one or more diseases.

11 Claims, 18 Drawing Sheets

(56) References Cited

OTHER PUBLICATIONS

Mediomic's L-Tryptophan Assay Kit, available as of Jun. 6, 2006. Web. <http://search.cosmobio.co.jp/cosmo_search_p/search_gate2/docs/MDM_/111001B.20060615.pdf> Accessed on Mar. 25, 2015 (hereinafter referred to as Mediomics').*

Lamont et al., Measurement of Individual vs. Total Antioxidant, Clinical Chemistry, 43(5), (1997), p. 852-854.*

Bener et al., Development of a Low-Cost Optical Sensor for Cupric Reducing Antioxidant Capacity Measurement in Food Extracts, Anal. Chem., 82, (2010) (Published online Apr. 2010), p. 4252-4258.*

Mayai et al., Changes in concentrations of urinary proteins after physical exercise, Acta Med Okayama, (1990), 44(5), p. 263-266.*

Demir et al., Effect of Exercise on Lipid peroxidation, Acta Medica, (2001), 44(1), p. 41-42.*

Anzhong et al, The effect of swimming on the concentration of urinary superoxide dismutase, Chinese Journal of Sports Medicine, Mar. 1993.*

USPTO; Restriction requirement dated Oct. 17, 2017 in U.S. Appl. No. 14/904,274.

PCT: International Search Report dated Feb. 23, 2012 in US2011044786.
PCT: IPRP dated Jan. 30, 2012 in US2011044786.
PCT: Written Opinion dated Feb. 23, 2012 in US2011044786.
PCT: International Search Report dated Oct. 5, 2016 in US201629725.
PCT: Written Opinion dated Oct. 5, 2016 in US201629725.
PCT: IPRP dated Oct. 31, 2017 in US201629725.
PCT: Written Opinion dated Jun. 16, 2016 in US201623702.
PCT: International Search Report dated Jun. 16, 2016 in US201623702.
PCT: IPRP dated Sep. 26, 2017 in US201623702.
PCT: Search Report dated Nov. 4, 2014 in US201442464.
PCT: Written Opinion dated Nov. 4, 2014 in US201442464.
PCT: IPRP dated Oct. 2, 2014 in US201442464.
PCT: International Search Report dated Mar. 3, 2015 in US2014053836.
PCT: Written Opinion dated Feb. 2, 2015 in US2014053836.
PCT: IPRP dated Mar. 8, 2016 in US2014053836.

* cited by examiner

Taking Wellness to the Next Level:
Get to Know Your Health Equater™ Assessment Profile

*Your Health Equater Assessment Profile provides a snapshot of healthy and unhealthy processes occurring in your body. Along with other measurements, you and your Wellness Consultant are now better able to understand your wellness status. "Wellness" means a general state of physical health and well-being.*

*The Health Equater Assessment Profile identifies some general health risks. You will learn about conditions present in your body that may increase your risk of disease, but have absolutely no symptoms. Scientific evidence shows that certain conditions – oxidative stress, low-grade inflammation, reduced antioxidant capacity – are strongly associated with some diseases. The Health Equater Assessment Profile analyzes your urine for five different biomarkers. A biomarker is a substance measured in urine that is associated with the risk of disease.*

*The Health Equater Assessment Profile is the first product that quickly, easily, and accurately measures levels of oxidative stress, low-grade inflammation, and antioxidant capacity. Armed with the information provided by the Health Equater Assessment Profile, you are taking important first steps toward understanding your health. See page 3 for your individualized wellness report and page 4 for some ways to improve your health.*

How Can the Health Equater™ Assessment Profile Improve Your Health?

Information is power, especially when it comes to your health. The Health Equater Assessment Profile provides a wealth of information that you and your Wellness Consultant can use as a starting point to improve your overall health and reduce your risk of some serious illnesses. Working with your Wellness Consultant, you can explore a wide variety of activities that may quickly make a measurable difference. It is not important how or where you begin. What is most important is that you are making a fresh start. You and your Wellness Consultant can track your progress with another Health Equater Assessment Profile in a few weeks or months. The Health Equater Assessment Profile helps you take wellness to the next level!

Oxidative Stress

Oxidative stress is a condition of imbalance between the body's natural protective mechanisms and high levels of reactive oxygen species, such as free radicals. A free radical is a naturally occurring oxygen-containing substance that, when present in small quantities, helps the cells in the body communicate with each other. High levels of free radicals damage the body's DNA, proteins, and fats and are implicated in heart disease, cancer, diabetes, stroke, obesity, depression, and nervous system diseases, such as Alzheimer's disease and Parkinson's disease. In young, healthy, and physically active persons, free radicals are naturally kept in check by strong antioxidant defense mechanisms. However, in persons with weaker antioxidant responses, high levels of free radicals overwhelm the body's ability to destroy them, causing damage to cells and risk of serious diseases. The Health Equater Assessment Profile analyzes your urine for two biomarkers of oxidative stress.

Inflammation

There is a very strong relationship between low-grade (or chronic) inflammation and metabolic syndrome (a group of risk factors for heart disease, diabetes, and stroke), cardiovascular disease, cancer, diabetes, and other serious conditions. Physicians may even recommend taking low-dose aspirin (an anti-inflammatory medication) once daily to lower the risk of heart disease, stroke, and some cancers. The Health Equater Assessment Profile analyzes your urine for two biomarkers of inflammation.

Total Antioxidant Capacity

The body has many effective, built-in antioxidant systems that protect against oxidative stress. Different substances, such as vitamins, minerals, enzymes, and proteins, prevent damage to cells and act as a natural antioxidant defense system. The condition of oxidative stress occurs when levels of free radicals overwhelm the body's natural antioxidant capacity. The Health Equater Assessment Profile measures your body's antioxidant capacity using the TAC (Total Antioxidant Capacity) assay.

*These statements have not been evaluated by the Food and Drug Administration. This product is not intended to diagnose, treat, cure, or prevent any disease.*

FIGURE 5B

How Healthy Am I? — Oxidative Stress

Your individualized report is interpreted in the next four pages. See page six for information on ways to improve your health.

Oxidative Stress

*Oxidative stress is a condition where reactive oxygen species, such as free radicals, are produced faster than they are neutralized by the body's natural protective mechanisms. High levels of free radicals are very harmful and are associated with several serious diseases. Your urine was tested for two biomarkers of oxidative stress. A biomarker is a substance in the urine that indicates risk for disease. These oxidative stress biomarkers may increase briefly after strenuous exercise, which is normal. However, persistently elevated levels of oxidative stress biomarkers are associated with poor health.*

*One oxidative stress biomarker is TBARS (thiobarbituric acid reactive substances), which is a useful way to screen for oxidative stress and increased risk of certain conditions, like stroke, diabetes, heart disease, and lung disease. TBARS are a group of substances that indicate the presence of cell damage caused by oxidative stress.*

*MDA (malondialdehyde), a highly specific and accurate oxidative stress biomarker, is also measured in the Health Equater™ Assessment Profile. MDA is a toxic substance that is naturally produced when certain fats are broken down and used by the body. Increased levels of MDA are linked to heart attack, stroke, diabetes, risk factors for heart disease and diabetes (increased insulin resistance, high blood pressure, increased triglycerides, increased blood sugar, smoking), lung disease, Parkinson's disease, Alzheimer's disease, and depression.*

Your Results:

TBARS

TBARS is a well-established biomarker of oxidative stress. The concentration of TBARS in your urine is greatly increased and is well outside the healthy range. Elevated TBARS levels suggest a greatly increased risk of heart disease, type 2 diabetes, and lung disease. Studies have shown increased TBARS levels in persons with cardiovascular disease, atherosclerosis, stroke, type 2 diabetes, asthma/chronic obstructive lung disease (COPD), and other medical conditions.

You indicated that you smoke, which is strongly associated with increased oxidative stress. If you continue to smoke, your level of oxidative stress and risk of disease, which are already very high, will increase even more.

MDA

MDA is a toxic substance that is a highly specific biomarker of oxidative stress. The level of MDA in your urine is greatly increased and outside the healthy range, which suggests you have a very high and unhealthy level of oxidative stress. MDA is increased in persons who have had a heart attack or stroke and in persons with diabetes, Parkinson's disease, Alzheimer's disease, and depression. Greatly elevated levels of MDA are associated with increased risk of metabolic syndrome and other risk factors for heart disease and diabetes.

You are a smoker, which contributes to your very high levels of MDA. If you continue to smoke, your already high levels of oxidative stress and risk of disease will increase even more.

*These statements have not been evaluated by the Food and Drug Administration. This product is not intended to diagnose, treat, cure, or prevent any disease.*

FIGURE 5C

How Healthy Am I?

Inflammation

Inflammation is a healthy and normal way for the body to begin healing after an infection, injury, or exposure to harmful substances. However, when inflammation lasts a long time, the normal functions of cells in the body may be altered. Inflammation may occur at such low levels that you are not even aware that it is taking place. This low-grade inflammation may be linked to the development of metabolic syndrome, heart disease, stroke, cancer, diabetes, and other serious disorders. The Health Equater™ Assessment Profile analyzes your urine for two biomarkers of inflammation: urinary protein and nitric oxide substances (NOx).

Healthy people usually have extremely low levels of protein in their urine. However, low-grade inflammation increases the levels of protein in the urine, and persistently increased urinary protein may predict the development of some diseases. The Health Equater Assessment Profile uses a highly accurate and specific method to test for protein in your urine. Your urine was also tested for nitric oxide byproducts (NOx), which are well-established biomarkers of low-grade inflammation. High levels of NOx suggest low-grade inflammation and increased risk of cardiovascular disease, diabetes, and cancer.

Your Results:

Urinary Protein

The concentration of protein in your urine is greatly increased. Even though this test does not measure very high protein levels that are considered diagnostic for disease, the amount of protein in your urine is well above the desired range for healthy adults. Inflammation increases protein in the urine and increases the risk of serious cardiovascular disease and kidney failure. The presence of protein in the urine strongly predicts the occurrence of heart attack, stroke, and other cardiovascular events, as shown by studies that monitored the health of thousands of healthy adults for 10 years.

NOTE: After exercising, it is normal that excretion of protein in your urine will increase for a short time, especially if you are younger than 30. However, if you have type 2 diabetes and/or hypertension, even small amounts of protein in the urine may predict the development of heart attack or stroke. You may consider taking the Health Equater™ Assessment Profile again at another time. If you continue to have increased levels of protein in your urine, consultation with a physician may be appropriate.

Nitric Oxide Metabolites

Your urine was tested for nitric oxide byproducts (NOx), and the results indicate that your NOx levels are greatly increased. The greatly increased levels of NOx in your urine suggest low-grade inflammation and increased risk of some diseases. Levels of NOx are increased in metabolic syndrome, diabetes, some types of cancer, osteoporosis, prostatitis, and multiple sclerosis.

NOTE: If you have recently eaten highly processed meat products containing nitrates, the levels of NOx in your urine may be falsely elevated. You may choose to retake the Health Equater Assessment Profile at another time.

These statements have not been evaluated by the Food and Drug Administration. This product is not intended to diagnose, treat, cure, or prevent any disease.

FIGURE 5D

Total Antioxidant Capacity

How Healthy Am I?

Total Antioxidant Capacity

The body possesses many strong, natural ways of fighting the harmful effects of oxidative stress. This protective mechanism is called antioxidant capacity. When the body's antioxidant capacity is very low or when levels of free radicals are very high, oxidative stress can occur. Antioxidant capacity declines with age and sedentary behavior. Reduced antioxidant capacity is also associated with obesity, breast cancer, viral infection, and other medical conditions. The Health Equater™ Assessment Profile analyzed your urine for your total antioxidant capacity (TAC). TAC is a highly accurate test that measures a wide range of antioxidants and provides information on your body's resistance to oxidative stress.

BMI

Body mass index (BMI) is determined from your height and weight and provides an estimate of body fat. Although elevated BMI increases the risk of diseases related to overweight and obesity, BMI is not a useful risk predictor when used alone. For example, BMI may overestimate body fat in athletes with muscular bodies and underestimate body fat in older persons because of muscle loss that occurs with aging. The BMI is most helpful when used together with other measures of health, which is why the Health Equater Assessment Profile analyzes your urine for biomarkers of oxidative stress, inflammation, and total antioxidant capacity.

Your Results:

Total Antioxidant Capacity

Your urine was analyzed for antioxidants using the TAC (Total Antioxidant Capacity) test, which measures your body's overall antioxidant capacity. Your TAC level is low, which indicates that you have reduced antioxidant capacity and may be less resistant to oxidative stress and the diseases associated with it.

Body Mass Index

Body Mass Index

Your BMI is between 30.0 and 34.9, which puts you in the obese category. Based only on your BMI, you are at significantly increased risk of obesity-related diseases, such as metabolic syndrome, atherosclerosis, stroke, type 2 diabetes, and some cancers. However, BMI only gives you a general estimate of your risk of certain diseases. The Health Equater Assessment Profile provides more specific information about your overall state of health.

These statements have not been evaluated by the Food and Drug Administration. This product is not intended to diagnose, treat, cure, or prevent any disease.

FIGURE 5E

Work with Your Wellness Consultant to Improve Your Health

Your Health Equater Assessment Profile Results

Now is a great time to roll up your sleeves and improve your health! According to the information that you provided, you smoke and are overweight. In addition, your Health Equater Assessment Profile results indicate increased levels of oxidative stress and inflammation. The combined effects of being overweight, smoking, and the increased levels of oxidative stress and inflammation suggest that unhealthy things are happening in your body. You are at substantial risk of heart disease, diabetes, cancer, and other serious illnesses.

In Conclusion

The choices you make about your diet are very important to your overall health. Major medical organizations recommend healthy eating as one way to reduce the risk of heart disease, stroke, diabetes, and cancer. Diets high in fruits, vegetables, whole grains, fish, and moderate amounts of lean protein and reduced-fat dairy products are good for you and can help you maintain a healthy weight. Foods like fish oils, nuts, green tea, cocoa, berries, flaxseed oil, and olive oil may improve measures of oxidative stress, inflammation, and total antioxidant capacity. The Mediterranean Diet, which consists of fish, whole grains, olive oil, nuts, beans, and legumes, is a particularly healthy choice.

Physical activity is another important part of good health. Exercise may help prevent cardiovascular disease, diabetes, and cancer. Regular exercise helps maintain a healthy weight and has positive anti-inflammatory effects. Your Wellness Consultant can help you choose the type of exercise that is right for you. An ideal exercise plan consists of regular activities that burn calories (eg, walking) as well as activities that build muscle (eg, walking with light weights).

Even if you lead a very active life, it is important to make changes in your current exercise plan slowly and don't do too much all at once. Find times in your day to increase your level of activity, like parking farther away from the grocery store, taking the stairs at work instead of the elevator, or walking for 30 minutes after dinner. If you are already exercising regularly, good for you! Work with your Wellness Consultant to find ways to vary your routine and make the most of your workouts.

Start Now to Take Wellness to the Next Level

Your Wellness Professional can gauge your overall health and improve areas that need attention. There is no time like the present to develop a plan to lose weight, exercise more, and stop smoking. Your Health Equater Assessment Profile indicates that your levels of oxidative stress and inflammation are increased. Even if you feel healthy now, you may want to consult with a medical professional about your increased risk of diseases related to oxidative stress, low-grade inflammation, overweight, and smoking.

*These statements have not been evaluated by the Food and Drug Administration. This product is not intended to diagnose, treat, cure, or prevent any disease.*

FIGURE 5F

Taking Wellness to the Next Level:
Get to Know Your Health Equater™ Assessment Profile

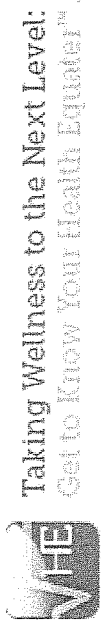

*Your Health Equater Assessment Profile provides a snapshot of healthy and unhealthy processes occurring in your body. Along with other measurements, you and your Wellness Consultant are now better able to understand your wellness status. "Wellness" means a general state of physical health and well-being.*

*The Health Equater Assessment Profile identifies some general health risks. You will learn about conditions present in your body that may increase your risk of disease, but have absolutely no symptoms. Scientific evidence shows that certain conditions – oxidative stress, low-grade inflammation, reduced antioxidant capacity – are strongly associated with some diseases. The Health Equater Assessment Profile analyzes your urine for five different biomarkers. A biomarker is a substance measured in urine that is associated with the risk of disease.*

*The Health Equater Assessment Profile is the first product that quickly, easily, and accurately measures levels of oxidative stress, low-grade inflammation, and antioxidant capacity. Armed with the information provided by the Health Equater Assessment Profile, you are taking important first steps toward understanding your health. See page 3 for your individualized wellness report and page 4 for some ways to improve your health.*

How Can the Health Equater™ Assessment Profile Improve Your Health

Information is power, especially when it comes to your health. The Health Equater Assessment Profile provides a wealth of information that you and your Wellness Consultant can use as a starting point to improve your overall health and reduce your risk of some serious illnesses. Working with your Wellness Consultant, you can explore a wide variety of activities that may quickly make a measurable difference. It is not important how or where you begin. What is most important is that you are making a fresh start. You and your Wellness Consultant can track your progress with another Health Equater Assessment Profile in a few weeks or months. The Health Equater Assessment Profile helps you take wellness to the next level!

Oxidative Stress

Oxidative stress is a condition of imbalance between the body's natural protective mechanisms and high levels of reactive oxygen species, such as free radicals. A free radical is a naturally occurring oxygen-containing substance that, when present in small quantities, helps the cells in the body communicate with each other. High levels of free radicals damage the body's DNA, proteins, and fats and are implicated in heart disease, cancer, diabetes, stroke, obesity, depression, and nervous system diseases, such as Alzheimer's disease and Parkinson's disease, in young, healthy, and physically active persons; free radicals are naturally kept in check by strong antioxidant defense mechanisms. However, in persons with weaker antioxidant responses, high levels of free radicals overwhelm the body's ability to destroy them, causing damage to cells and risk of serious diseases. The Health Equater Assessment Profile analyzes your urine for two biomarkers of oxidative stress.

Inflammation

There is a very strong relationship between low-grade (or chronic) inflammation and metabolic syndrome (a group of risk factors for heart disease, diabetes, and stroke), cardiovascular disease, cancer, diabetes, and other serious conditions. Physicians may even recommend taking low-dose aspirin (an anti-inflammatory medication) once daily to lower the risk of heart disease, stroke, and some cancers. The Health Equater Assessment Profile analyzes your urine for two biomarkers of inflammation.

Total Antioxidant Capacity

The body has many effective, built-in antioxidant systems that protect against oxidative stress. Different substances, such as vitamins, minerals, enzymes, and proteins, prevent damage to cells and act as a natural antioxidant defense system. The condition of oxidative stress occurs when levels of free radicals overwhelm the body's natural antioxidant capacity. The Health Equater Assessment Profile measures your body's antioxidant capacity using the TAC (Total Antioxidant Capacity) assay.

*These statements have not been evaluated by the Food and Drug Administration. This product is not intended to diagnose, treat, cure, or prevent any disease.*

FIGURE 6B

How Healthy Am I?

Oxidative Stress

Your individualized report is interpreted in the next four pages. See page six for information on ways to improve your health.

Oxidative Stress

*Oxidative stress is a condition where reactive oxygen species, such as free radicals, are produced faster than they are neutralized by the body's natural protective mechanisms. High levels of free radicals are very harmful and are associated with several serious diseases. Your urine was tested for two biomarkers of oxidative stress. A biomarker is a substance in the urine that indicates risk for disease. These oxidative stress biomarkers may increase briefly after strenuous exercise, which is normal. However, persistently elevated levels of oxidative stress biomarkers are associated with poor health.*

*One oxidative stress biomarker is TBARS (thiobarbituric acid reactive substances), which is a useful way to screen for oxidative stress and increased risk of certain conditions, like stroke, diabetes, heart disease,*

*and lung disease. TBARS are a group of substances that indicate the presence of cell damage caused by oxidative stress.*

*MDA (malondialdehyde), a highly specific and accurate oxidative stress biomarker, is also measured in the Health Equater™ Assessment Profile. MDA is a toxic substance that is naturally produced when certain fats are broken down and used by the body. Increased levels of MDA are linked to heart attack, stroke, diabetes, risk factors for heart disease and diabetes (increased insulin resistance, high blood pressure, increased triglycerides, increased blood sugar, smoking), lung disease, Parkinson's disease, Alzheimer's disease, and depression.*

Your Results:

TBARS

TBARS is a well-established biomarker of oxidative stress. The concentration of TBARS in your urine is moderately increased and outside the healthy range. Elevated TBARS levels suggest an increased risk of heart disease, type 2 diabetes, and lung disease. Studies have shown increased TBARS levels in persons with cardiovascular disease, atherosclerosis, stroke, type 2 diabetes, asthma/chronic obstructive lung disease (COPD), and other medical conditions.

You indicated that you do not smoke, which is a very healthy lifestyle choice because smoking is strongly associated with increased oxidative stress.

MDA

MDA is a toxic substance that is a highly specific biomarker of oxidative stress. The level of MDA in your urine is moderately increased and outside the healthy range. Elevated MDA levels indicate increased oxidative stress, which is not healthy. MDA is increased in persons who have had a heart attack or stroke and in persons with diabetes, Parkinson's disease, Alzheimer's disease, and depression. Elevated levels of MDA are associated with increased risk of metabolic syndrome and other risk factors for heart disease and diabetes.

You do not smoke, which is good because smoking is likely to increase your MDA level and risk of disease even more.

*These statements have not been evaluated by the Food and Drug Administration. This product is not intended to diagnose, treat, cure, or prevent any disease.*

FIGURE 6C

How Healthy Am I?

Inflammation

Inflammation is a healthy and normal way for the body to begin healing after an infection, injury, or exposure to harmful substances. However, when inflammation lasts a long time, the normal functions of cells in the body may be altered. Inflammation may occur at such low levels that you are not even aware that it is taking place. This low-grade inflammation may be linked to the development of metabolic syndrome, heart disease, stroke, cancer, diabetes, and other serious disorders. The Health Equater™ Assessment Profile analyzes your urine for two biomarkers of inflammation: urinary protein and nitric oxide substances (NOx).

Inflammation

Healthy people usually have extremely low levels of protein in their urine. However, low-grade inflammation increases the levels of protein in the urine, and persistently increased urinary protein may predict the development of some diseases. The Health Equater Assessment Profile uses a highly accurate and specific method to test for protein in your urine. Your urine was also tested for nitric oxide byproducts (NOx), which are well-established biomarkers of low-grade inflammation. High levels of NOx suggest low-grade inflammation and increased risk of cardiovascular disease, diabetes, and cancer.

Your Results:

Urinary Protein

The concentration of protein in your urine is low. This is healthy because inflammation increases protein in the urine and increases the risk of serious cardiovascular disease and kidney failure. The presence of protein in the urine strongly predicts the occurrence of heart attack, stroke, and other cardiovascular events, as shown by studies that monitored the health of thousands of healthy adults for 10 years.

Nitric Oxide Metabolites

Your urine was tested for nitric oxide byproducts (NOx), and the results indicate that your NOx levels are low and within the healthy range. Elevated NOx in the urine suggests the presence of low-grade inflammation, which is present in metabolic syndrome, diabetes, some types of cancer, osteoporosis, prostatitis, and multiple sclerosis.

*These statements have not been evaluated by the Food and Drug Administration. This product is not intended to diagnose, treat, cure, or prevent any disease.*

FIGURE 6D

How Healthy Am I?

Total Antioxidant Capacity

*The body possesses many strong, natural ways of fighting the harmful effects of oxidative stress. This protective mechanism is called antioxidant capacity. When the body's antioxidant capacity is very low or when levels of free radicals are very high, oxidative stress can occur. Antioxidant capacity declines with age and sedentary behavior. Reduced antioxidant capacity is also associated with obesity, breast cancer, viral infection, and other medical conditions. The Health Equater™ Assessment Profile analyzed your urine for your total antioxidant capacity (TAC). TAC is a highly accurate test that measures a wide range of antioxidants and provides information on your body's resistance to oxidative stress.*

BMI

*Body mass index (BMI) is determined from your height and weight and provides an estimate of body fat. Although elevated BMI increases the risk of diseases related to overweight and obesity, BMI is not a useful risk predictor when used alone. For example, BMI may overestimate body fat in athletes with muscular bodies and underestimate body fat in older persons because of muscle loss that occurs with aging. The BMI is most helpful when used together with other measures of health, which is why the Health Equater Assessment Profile analyzes your urine for biomarkers of oxidative stress, inflammation, and total antioxidant capacity.*

Total Antioxidant Capacity

Your Results:

Total Antioxidant Capacity

Your urine was analyzed for antioxidants using the TAC (Total Antioxidant Capacity) test, which measures your body's overall antioxidant capacity. Your TAC level is average, which indicates that your level of antioxidant capacity is good.

Body Mass Index

Body Mass Index

Your BMI is between 25.0 and 29.9, which puts you in the overweight category. Based only on your BMI, you are at increased risk of obesity-related diseases, such as metabolic syndrome, atherosclerosis, stroke, type 2 diabetes, and some cancers. However, BMI only gives a general estimate of your risk of certain diseases. The Health Equater Assessment Profile provides more specific information about your overall state of health.

*These statements have not been evaluated by the Food and Drug Administration. This product is not intended to diagnose, treat, cure, or prevent any disease.*

FIGURE 6E

Work with Your Wellness Consultant to Improve Your Health

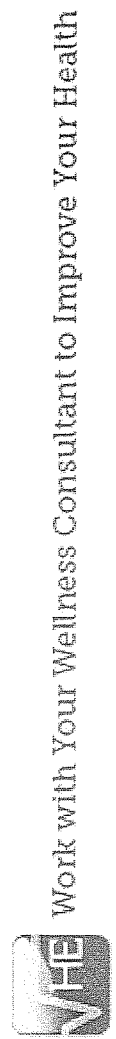

Your Health Equater™ Assessment Profile Results

Your Health Equater Assessment Profile results indicate that you have low levels of oxidative stress and inflammation. You do not smoke, which is good. You and your Wellness Consultant can take a close look at your diet and level of activity and develop a practical plan to help you lose weight.

In Conclusion

The choices you make about your diet are very important to your overall health.

Major medical organizations recommend healthy eating as one way to reduce the risk of heart disease, stroke, diabetes, and cancer. Diets high in fruits, vegetables, whole grains, fish, and moderate amounts of lean protein and reduced-fat dairy products are good for you and can help you maintain a healthy weight. Foods like fish oils, nuts, green tea, cocoa, berries, flaxseed oil, and olive oil may improve measures of oxidative stress, inflammation, and total antioxidant capacity. The Mediterranean Diet, which consists of fish, whole grains, olive oil, nuts, beans, and legumes, is a particularly healthy choice.

Physical activity is another important part of good health. Exercise may help prevent cardiovascular disease, diabetes, and cancer. Regular exercise helps maintain a healthy weight and has positive anti-inflammatory effects. Your Wellness Consultant can help you choose the type of exercise that is right for you. An ideal exercise plan consists of regular activities that burn calories (eg, walking) as well as activities that build muscle (eg. walking with light weights).

Even if you lead a very active life, it is important to make changes in your current exercise plan slowly and don't do too much all at once. Find times in your day to increase your level of activity, like parking farther away from the grocery store, taking the stairs at work instead of the elevator, or walking for 30 minutes after dinner. If you are already exercising regularly, good for you! Work with your Wellness Consultant to find ways to vary your routine and make the most of your workouts.

Start Now to Take Wellness to the Next Level

Your Wellness Consultant can gauge your overall health and help you improve areas that need attention. You are moving in the right direction because the results of your Health Equater Assessment Profile indicate your levels of oxidative stress and inflammation are low for now, and you do not smoke. There is no time like the present to assess your diet and activity level, which together will help you lose weight so that you can enjoy wellness and good health.

These statements have not been evaluated by the Food and Drug Administration. This product is not intended to diagnose, treat, cure, or prevent any disease.

FIGURE 6F

WELLNESS PANEL

This application is a U.S. National Phase under 35 U.S.C. § 371 of International Application No. PCT/US2011/044786, filed Jul. 21, 2011, which claims priority from U.S. Provisional Patent Application No. 61/367,486, filed Jul. 26, 2010.

BACKGROUND OF THE INVENTION

1. Technical Field

The present invention relates to assays and panels for detection of biomarkers, with the term "biomarker" referring to an analyte in a body fluid that is associated with a physiological condition and/or the presence or risk of contracting one or more diseases. In particular, the present invention relates to non-invasive detection of biomarkers in urine.

2. Background Art

It is well established in the scientific literature that certain physiological conditions, including oxidative stress and/or chronic inflammation, play key roles in several pathological disturbances such as atherosclerosis, obesity, diabetes, neurodegenerative diseases and cancer. Diet, lifestyle, exercise, as well as certain drugs have anti-inflammatory and/or anti-oxidant activity. Indeed, the market for antioxidants alone runs to billions of dollars per year. Many biomarkers for inflammation, oxidative stress, and anti-oxidant activity have been reported in the literature.

In contrast to the assessment of wellness or relative health, or for the assessment of the risk of development of disease(s), traditional tests are designed and employed to diagnose specific diseases, with an increasing emphasis on early diagnosis. Some available tests do analyze for some substances, such as cholesterol, lipoproteins, and CRP (c-reactive protein), albumin/creatinine ratio, and some other "risk factors" for specific diseases, e.g. cardiovascular disease. But, the disease-specific application of these few pre-symptomatic tests is still consistent with traditional medicine's focus on biomarkers for the diagnosis of specific disease For example, although chronic inflammation is associated with a significant increase in the risk for certain cancers, and regular use of drugs or dietary agents with anti-inflammatory activity have been proven to reduce the risk for such cancers, traditional clinical laboratories and clinicians do not monitor biomarkers for inflammation as risk factors for cancer.

Some "esoteric laboratories" offer a large number of tests such as cytokine assays, mostly using blood samples, to test for many reported biomarkers associated with disease(s) or disease risk. A few internet-based companies offer products that are purported to provide for the qualitative determination of oxidative stress biomarkers such as TBARS (thiobarbituric acid reactive substances) or other tests for biomarkers associated with oxidative stress (e.g. isoprostanes) in urine.

However, with the exception of the disease-specific (almost exclusively related to cardiovascular disease) application of the few examples cited above, at present none are readily available to individuals seeking to determine how healthy (low inflammation, low oxidative stress, high anti-oxidant activity) they are. As a specific example, the currently available CRP test only interprets the level of CRP as a marker for cardiovascular risk.

A few companies offer a wide range of exotic tests for human physiological biomarkers. For example, Genova Diagnostics offers an inflammation panel comprised of 3 inflammatory biomarkers (hsCRP, homocysteine and fibrinogen) in a blood sample, and an Oxidative Stress 2.0 blood test panel comprised of 10 biomarkers, one of which is lipid hydroperoxides. However, typically these tests are run either individually or in panels on blood samples and almost always require the samples be sent to a core laboratory. The latter requirement introduces several undesirable characteristics, including: the time, effort and cost of collection and transport of the specimens, the significant potential for ex vivo changes in the level(s) of the analytes that may arise either from the decomposition of an analyte or the artifactual generation of additional analyte from precursors in a sample. Such artifactual ex vivo changes in the levels of analytes are particularly well known in the case of oxidative stress biomarkers, but can also occur for inflammatory biomarkers in blood or urine specimens. For example, isoprostanes, which are well-studied biomarkers of oxidative stress, are rapidly generated ex vivo by the action of reactive oxygen species on arachidonic acid present in blood samples; and the level of protein in a urine sample may artifactually increase within hours at room temperature due to bacterial growth.

For example, U.S. Pat. No. 6,953,666 to Kinkade, Jr., et al. discloses methods and compositions for detecting the presence of oxidized derivatives of amino acids in proteins as biomarkers of oxidative stress. In principle, the biomarker can be any amino acid that has undergone oxidation (or other modification, e.g. dityrosine, nitrotyrosine which is produced by the reaction of tyrosine with peroxynitrite, or chloro-tyrosine, which is produced by the action of myeloperoxidase and is an inflammatory biomarker). Emphasis in Kinkade, Jr., et al. is given to oxidized sulfur- or selenium-containing amino acids (SSAA). Oxidized SSAA are amino acids in which the sulfur or selenium moiety has been oxidized to some oxidation state. Oxidized SSAA include, but are not limited to, cysteine, cystine, methionine, selenomethionine, selenocystine and selenocysteine in their various possible oxidation states. Typically, an ELISA assay is provided for quantification of these biomarkers.

U.S. Pat. No. 6,852,541 to Obayan, et al. discloses an assay for testing oxidative stress of a subject by measurement of oxidants in biological fluids such as urine, plasma, bioreactor medium and respiratory aspirants. There is provided a method of determining oxidative stress in a mammalian subject. The method comprises: obtaining a sample of a biological fluid from the subject; mixing the biological fluid with a ferrous reaction reagent; incubating the biological fluid and the reaction reagent; and detecting a colored reaction product. There is further provided a ferrous reaction reagent suitable for use in assaying oxidative stress, said reaction reagent comprising 2-deoxyglucose, TBA, EDTA, and ferrous sulfate, and being substantially free of ascorbic acid.

U.S. Pat. No. 7,288,374 to Pincemail, et al. discloses a process for detecting oxidative stress in a sample and to a kit for this implementation. According to one embodiment, the Pincemail, et al. invention provides a method for the detection of oxidative stress in an individual carrying a risk factor for oxidative stress comprising determining the risk factor for oxidative stress of said individual; selecting at least two oxidative stress markers being increased or decreased for said risk factor relative to healthy individuals; and measuring the amount of said at least two oxidative stress markers in a sample obtained from said individual. Oxidative stress markers in the invention of Pincemail, et al. are detected from whole blood samples or samples containing components thereof.

U.S. Pat. No. 5,858,696 to Roberts, II et al. discloses a method of assessing oxidative stress in vivo by quantification of prostaglandin $F_2$-like compounds and their metabolites produced by a non-cyclooxygenase free radical catalyzed mechanism.

U.S. Pat. No. 5,912,179 to Alvarez, et al. discloses systems and methods for material analysis in which an organic sample (e.g., a foodstuff, tissue sample or petroleum product) is illuminated at a plurality of discrete wavelengths that are absorbed by fatty acid and fatty acid oxidation products in the sample. Measurements of the intensity of reflected or absorbed light at such wavelengths are taken, and an analysis of absorbance ratios for various wavelengths is performed. Changes in the reflection ratios are correlated with the oxidative state of fatty acids present in the material.

U.S. Pat. Nos. 6,096,556 and 6,133,039 disclose a non-invasive method for the determination of oxidative stress in a patient by urinalysis. The method comprises quantifying the level of o,o'-dityrosine in a sample of the urine of the patient and comparing with the corresponding level of the compound in a normal or control sample, whereby a substantially elevated level of said o,o'-dityrosine is indicative of oxidative stress in the patient.

U.S. Pat. No. 6,541,265 to Leeuwenburgh discloses methods and systems for testing a substance for inflammatory or oxidant properties under acute inflammatory conditions characterized by increased levels of redox-active metal ions. The method includes the steps of applying an eccentric exercise stimulus to a subject, thereby inducing a muscle injury; administering a substance of interest to the subject; measuring one or more biological markers of inflammation, oxidative stress, and muscle damage, or combinations thereof, within the subject; and correlating the measured value of the biological marker(s) with the inflammatory or oxidative properties of the substance administered. The systems of the subject invention include means for obtaining a biological sample from a subject, means for applying eccentric exercise stimulus to the subject; means for measuring the amount of the biological marker(s) within the biological sample; and means for correlating the measured amounts of the biological marker(s) with the inflammatory or oxidant properties of the substance administered.

U.S. Pat. No. 6,569,683 to Ochi, et al. discloses a diagnostic plot derived from the measurement of 82 assays that characterize two key parameters that significantly contribute to an individual's health status. These two parameters are oxidative stress profile (OSP) and antioxidant profile. Each of the 82 assays is complimentary with other assays of the profile, thus providing either confirmation information or the synthesis of new information. The diagnostic plot, developed to interpret the assay data, which provides information about oxidative damage and antioxidant protection, consists of four quadrants, each with noticeable characteristics. By visually assessing the position of a patient's OSP status, in comparison to reference OSP values in the four quadrants constituting the diagnostic plot, physicians and other health care professionals can provide sound advice to their patients regarding dietary and life style changes one need to adhere for prevention of oxidative stress-related diseases as well as postponing premature aging processes.

Vassalle et al. (Vassalle C, Pratali L, Boni C, Mercuri A, Ndreu R. An oxidative stress score as a combined measure of the pro-oxidant and anti-oxidant counterparts in patients with coronary artery disease. Olin Biochem. 41:1162-7 (2008)) have report an "oxidative stress index" in which tests for both the oxidative damage and antioxidant components of a blood sample are performed and the Oxidative-INDEX is computed based on a formula employing both components.

U.S. Patent Application Publication No. 2007/0054347 to Rosendahl, et al. discloses an optical analyzer for measuring an oxidative stress component in a patient, having a light source and a light detector used for measuring an optical property of a medium and generating optical measurement data. A processor analyzes the optical measurement data and generates a value for one or more oxidative stress component in the form of a redox signature for the patient. Probability data of the presence of an oxidative stress dependent disease can be calculated. By observing at least one additional clinical condition of the disease, a diagnosis using said at least one additional condition and said redox signature can be obtained.

U.S. Patent Application Publication No. 2010/0267037 to Westbrook, et al. discloses a method for detection of inflammatory disease in a subject that comprises assaying a test sample of peripheral blood from the subject for a marker of DNA damage. An elevated amount of the marker present in the test sample compared to control sample and this is described to be indicative of inflammatory disease activity, including sub-clinical inflammation. The method can be adapted for quantitatively monitoring the efficacy of treatment of inflammatory disease in a subject. Markers of DNA damage include single- and/or double-stranded breaks in leukocytes, oxidative DNA damage in leukocytes, or a marker of nitric oxide oxidative activity (protein nitrosylation in leukocytes). The inflammatory disease can be inflammatory bowel disease (ulcerative colitis or Crohn's disease). The invention is described as also being useful for detection of other types of inflammatory disease, such as non-immune intestinal inflammatory disease (diverticulitis, pseudomembranous colitis), autoimmune diseases (rheumatoid arthritis, lupus, multiple sclerosis, psoriasis, uveitis, vasculitis), or non-immune lung diseases (asthma, chronic obstructive lung disease, and interstitial pneumonitis).

The methods cited above typically require complex instrumentation and technically skilled operator, so that they are expensive and not suitable for widespread application. Further, as noted above, this typically requires that samples be transported to specialized locations capable of performing such analyses, which may result in alterations to the analyte(s).

Many devices have been developed to analyze for specific substances in biological specimens at the point of testing by employing dry chemical, microfluidic and/or immuno-chemical methods. Several such methods, which are in widespread use, are essentially dry chemistry tests involving test pads into which chemicals have been impregnated and which react relatively specifically with analytes in with biofluids, and the results of which can be read by optical or other methods. The analysis can involve simply visual comparison to the color of a reference chart, which is widely employed for the qualitative analysis of water in pools and spas and for the analysis of multiple disease-related analytes in urine and other body fluids. Semi-quantitative results may be obtained by the application of a device to measure the amount of color developed.

For example, U.S. Pat. No. 5,597,532 to Connolly discloses an apparatus for the optoelectronic evaluation of test paper strips for use in the detection of certain analytes in blood or other body fluids. The test strip comprises an elongated plastic part including a hinged portion to allow a first portion to be folded over a second portion. A series of layers of test strips are disposed between the folded over portions of the test strip. The test strip is configured such that the chemistry layers are placed in contacting engagement with one another, but not compressing one another. A reflectance photometer is provided and includes various features, including a lot number reader wherein if the test strip does not match the memory module, a test is not performed, and the user is instructed to insert a correct memory module.

U.S. Pat. Nos. 6,511,814 and 6,551,842 to Carpenter discloses a disposable, dry chemistry analytical system that is broadly useful for the detection of a variety of analytes present in biological fluids such as whole blood, serum, plasma, urine and cerebral spinal fluid. The invention discloses the use of the reaction interface that forms between two liquids converging from opposite directions within a bibulous material. The discovery comprises a significant improvement over prior art disposable, analytical reagent systems in that the detectable reactant zone is visually distinct and separate from the unreacted reagents allowing for the use of reaction indicators exhibiting only minor changes as well as extremely high concentrations of reactants. In addition, staged, multiple reagents can be incorporated. Whole blood can be used as a sample without the need for separate cell separating materials. Finally, the invention is useful for the detection of analytes in a broad variety of materials such as milk, environmental samples, and other samples containing target analytes.

U.S. Pat. No. 7,267,799 to Borich, et al. discloses an optical reading system, a universal testing cartridge, and a method of coupling optical reading systems. In a particular illustrative embodiment, the optical reading system includes a universal test cartridge receptor, test format determination logic, test criteria determination logic, and an optical reader module. The universal test cartridge receptor is responsive to a universal test cartridge having a test strip inserted therein. The test format determination logic determines an optical test format of the test strip. The test criteria determination logic determines an optical test criteria based upon the optical test format. The optical reader module is configured to capture an optical test image of the test strip.

U.S. Pat. No. 7,425,302 to Piasio, et al. discloses a lateral flow chromatographic assay format for the performance of rapid enzyme-driven assays. A combination of components necessary to elicit a specific enzyme reaction, which are either absent from the intended sample or insufficiently present therein to permit completion of the desired reaction, are predeposited as substrate in dry form together with ingredients necessary to produce a desired color upon occurrence of the desired reaction. The strip is equipped with a sample pad placed ahead of the substrate deposit in the flowstream, to which liquid sample is applied. The sample flows from the sample pad into the substrate zone where it immediately reconstitutes the dried ingredients while also intimately mixing with them and reacting with them at the fluid front. The fluid front moves rapidly into the final "read zone" wherein the color developed is read against predetermined color standards for the desired reaction. Pretreatment pads for the sample, as needed, (e.g. a lysing pad for lysing red blood cells in whole blood) are placed in front of the sample pad in the flow path as appropriate. The assay in the format of the invention is faster and easier to perform than analogous wet chemistry assays. Specific assays for glucose-6-phosphate dehydrogenase ("G-6PD"), total serum cholesterol, .beta.-lactamase activity and peroxidase activity are disclosed.

U.S. Pat. No. 7,521,260 to Petruno, et al. discloses an assay test strip includes a flow path, a sample receiving zone, a label, a detection zone that includes a region of interest, and at least one position marker. The at least one position marker is aligned with respect to the region of interest such that location of the at least one position marker indicates a position of the region of interest. A diagnostic test system includes a reader that obtains light intensity measurement from exposed regions of the test strip, and a data analyzer that performs at least one of (a) identifying ones of the light intensity measurements obtained from the test region based on at least one measurement obtained from the at least one reference feature, and (b) generating a control signal modifying at least one operational parameter of the reader based on at least one measurement obtained from the at least one reference feature.

U.S. Patent Application Publication No. 2009/0155921 to Lu, et al. discloses a method and apparatus for reading test strips such as lateral flow test strips as used for the testing of various chemicals in humans and animals. A compact and portable device is provided that may be battery powered when used remotely from the laboratory and, may store test data until it can be downloaded to another database. Motive power during scanning of the test strip is by means of a spring and damper that is wound by the operator during the insertion of a test strip cassette holder prior to test.

U.S. Patent Application Publication No. 2010/0311181 to Abraham, et al. discloses an assay reader system incorporating a conventional assay reader, for example a lateral flow reader, and an insert aligned with the readers sensor to detect an assay result. The insert may include a housing that defines a cavity to receive a removable barrier, wherein the removable barrier can be aligned between the sensor and the test strip. The barrier may include an optical window, and may be cleanable and/or disposable to maintain the accuracy of the reader. Test strips are introduced into the reader through a receiving port within the insert's housing. An air inlet on the insert further maintains the readers accuracy by allowing air to be tunneled over the housing to remove excess dust, debris, or the like.

The current methods described above for the assessment of oxidative stress, antioxidant capacity and inflammation have multiple drawbacks, including: some of the biomarkers (such as most oxidized lipids) are not stable for prolonged periods, even when stored frozen; some biomarkers (e.g. isoprostanes, widely regarded as biomarkers for oxidative stress) are generated ex vivo from the precursor (arachidonic acid) when some biological samples (particularly blood) are exposed to oxygen in the air; most require blood, which is invasive and requires a skilled person to collect the sample; most of the exotic testing laboratories have very high fees so that a multi-analyte assessment of healthy may cost from $2,000 to over $10,000, and typically requires a physician to analyze and interpret the data. Furthermore, some available tests, such as a commercial test marketed for monitoring lipid hydroperoxides in urine (it should be noted: free radicals themselves are so short-lived that they can't be directly measured in biofluids), do not employ any method to adjust or normalize the analysis for the relative concentration of the urine sample.

Furthermore, the levels of many of the biomarkers employed to assess oxidative stress, inflammation and/or antioxidant activity are impacted by and respond rapidly to factors unrelated to an individual's overall health and risk for contracting diseases. For example, the level of reactive oxygen species and consequently the levels of many biomarkers for oxidative stress, including isoprostanes and malondialdehyde, increase rapidly albeit transiently as a consequence of physical exercise. The level of nitric oxide metabolites (nitrate and nitrite) are transiently elevated following the consumption of processed foods containing nitrates as preservatives. The levels of urinary proteins can also be elevated by physical exercise. The level of isoprostanes in the urine is further influenced by the rapid metabolism of isoprostanes by the body, with the mechanism(s) and extent of metabolism of isoprostanes subject to considerable variation among individuals. Since uric acid is one of the major antioxidants present in blood and urine, the antioxidant activity of a sample is subject to variations in the rate of purine catabolism and also to dietary factors. For example, it has been reported that the primary mechanism responsible for the increase in antioxidant activity following consumption of apples is the uric acid derived from the apples. Hence, although there is significant evidence that the levels of specific individual biomarkers for oxidative stress, inflammation and/or antioxidant activity are related to health and disease risk based on extensive studies in experimental animals and in human populations, confounding factors such as those listed above are among the reasons why the application of these biomarkers for the assessment of the health and disease risk of individual humans has been very restricted.

Therefore, there is a need for a set of tests to quantify these biomarkers for these important physiological conditions, preferably including multiple biomarkers to significantly reduce confounding effects associated with the use of a single biomarker, that signal an individual's health and relative resistance to multiple diseases that can preferably be performed non-invasively for low cost and can provide accurate results regarding the health of the user.

SUMMARY OF THE INVENTION

The present invention provides for a panel for monitoring levels of biomarkers, including at least one inflammation monitoring test, at least one oxidative stress monitoring test, and at least one antioxidant activity monitoring test.

The present invention also provides for a method of monitoring an individual's health, by collecting a sample from the individual, applying the sample to an assay panel, performing inflammation monitoring test(s), oxidative stress monitoring test(s), and antioxidant activity monitoring test(s) in the panel, and thereby determining the levels of biomarkers related to inflammation, oxidative stress, and antioxidant activity and therefore determining the individual's relative health and susceptibility to certain diseases.

DESCRIPTION OF THE DRAWINGS

Other advantages of the present invention are readily appreciated as the same becomes better understood by reference to the following detailed description when considered in connection with the accompanying drawings wherein:

FIGS. 5A-5F are an example of a computer-generated report of the panel, wherein 5A is an overview of results, 5B describes tests in the panel, 5C-5E show text fields drawn from a computer database that are selected based on the relative levels for each of the biomarkers measured in the panel as well as other input factors (BMI and smoking status), and 5F shows fields summarizing the overall wellness of the individual based on the panel as well as descriptions of approaches to improving one's test results (and one's health), and for specific tests that are elevated, the fields also provide information on potential confounding variables, such as high nitrate levels due to consumption of some processed foods;

FIGS. 6A-6F are an example of a computer-generated report of the panel, wherein 6A is an overview of results, 6B describes tests in the panel, 6C-6E show text fields drawn from a computer database that are selected based on the relative levels for each of the biomarkers measured in the panel as well as other input factors (BMI and smoking status), and 6F shows fields summarizing the overall wellness of the individual based on the panel as well as descriptions of approaches to improving one's test results (and one's health), and for specific tests that are elevated, the fields also provide information on potential confounding variables, such as high nitrate levels due to consumption of some processed foods;

DETAILED DESCRIPTION OF THE INVENTION

Figure 1:
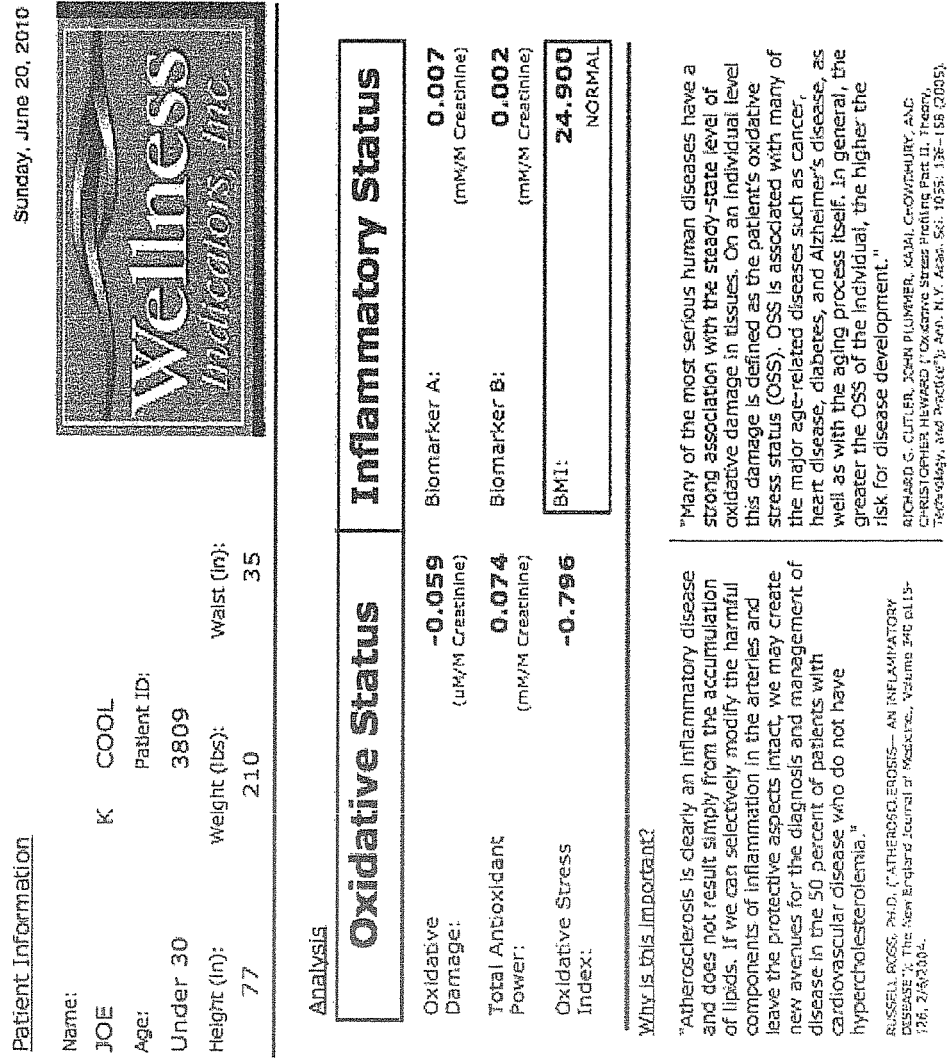
FIG. 1 is an example of a computer-generated report of the panel of the present invention.

The present invention provides a panel for monitoring, preferably non-invasively, the levels of biomarkers in human subjects. Most generally, the panel includes of a set of chemical, immunochemical and/or enzymatic assays or tests that can be used together for monitoring the levels of a set of biomarkers for three conditions: inflammation, oxidative stress, and anti-oxidant activity.

The term "assay" as used herein refers to a procedure that determines the amount of a particular constituent of a mixture or sample. "Assay" can interchangeably be used with the term "test" herein.

The term "biomarker" as used herein refers to a substance, such as, but not limited to, a protein, DNA sequence, RNA sequence, or other biological substance or substances (antioxidant activity tests can measure one specific substance or several—e.g. CUPRAC) that, when detected, indicates a particular healthy or unhealthy state of an individual.

The term "healthy" as used herein refers to a state of a person who is free from detectable disease and is in good health and has a relatively low risk of developing certain diseases. Such a person is considered "well".

The term "sample" as used herein refers to a biological sample from a human and is preferably urine. Other samples can be used in the present invention in the same manner described herein, such as, but not limited to, blood, plasma, tears, and cerebral spinal fluid (CSF). While urine is specifically referred to in the description herein, it should be understood that the other types of samples can be interchanged where appropriate and the invention is performed in the same manner. It should be noted that certain biomarkers can be present in one type of sample but not in others and that the biomarker measured can be specific to a urine sample, a blood sample, etc.

The panel of the present invention represents a significant departure from traditional clinical diagnosis, which seeks to diagnose diseases. The focus of the panel is to assess, preferably by a non-invasive quantitative test, how healthy or well an individual is by monitoring biomarkers for three factors, two of which are directly related to risk of disease (oxidative damage and inflammation) and one (antioxidant activity) which is inversely related to the risks of chronic diseases such as cancer, CVD, neurodegeneration, among others. A panel comprised of tests for one or more biomarkers for all three of these factors has not been previously used, especially in a urine test, nor has a panel comprised of tests for biomarkers for these conditions been combined previously with body mass index calculations and/or an individual's lifestyle.

The initial test panel is drawn from several hundred tests that have been reported in the literature for the measurement of oxidative damage, antioxidant power and inflammation (see Table 1 for summary of published biomarkers). Selection criteria include the reliability, selectivity, and sensitivity of each component test, the stability of the analyte(s) (e.g. relatively low reactivity with air and/or light once the specimen is collected, relatively low reactivity with other components of the sample such as reactivity with proteins to form adducts or the proteolytic degradation of protein analytes), and the ease of quantifying the analytes without the need for sophisticated equipment (e.g. LC/MS). The tests in the panel can be any single test below or combinations thereof.

TABLE 1

Possible Wellness Biomarkers and Assays

| Oxidative Damage: | Used as a biomarker in: | |
| --- | --- | --- |
| Broad measures of damage | Blood | Urine |
| TBARS | x | x |
| Organic Hydroperoxides | x | x |
| Protein Carbonyls | x | x |
| Measure of damage to specific molecules | Blood | Urine |
| Lipids | | |
| Malonaldehyde | x | x |
| 4-hydroxynonenal | x | x |
| Lipid hydroperoxides | x | x |
| Isoprostanes | x | x |
| Linoleic acid oxidation products | x | x |
| Proteins | | |
| Protein carbonyls | x | x |
| Nitrotyrosine | x | x |
| Nitrothiols | x | x |
| Up to 100 other oxidized AA | x | x |
| Nucleic acids | | |
| 8-hydroxy-deoxyguanosine | x | x |
| M1dG | x | x |
| Oxidized derivatives of ribose ring | x | x |
| Small molecules and ions | | |
| Selenium | x | x |
| GSH (glutathione) or GSSG (glutathione disulfide) and the GSH/GSSG ratio | x | x |

Antioxidant Power: Used as a biomarker in blood or urine:
Direct methods (measure reaction with a redox probe)
CUPRAC (cupric reducing antioxidant capacity)
Total Antioxidant Capacity (copper-bathocuprione method)
Indirect methods (measure resistance to oxidation of a probe by an added oxidizer)
FRAP (ferric reducing ability of plasma)
TRAP (total reactive antioxidant potential)
ORAC (oxygen radical absorbance capacity)
HORAC (hydroxyl radical antioxidant capacity)

TABLE 1-continued

Possible Wellness Biomarkers and Assays

Measurement of molecules that contribute to the total antioxidant capacity
GSH or GSSG and the GSH/GSSG ratio
Glutathione Peroxidase
Superoxide Dismutase
Uric acid
Ascorbic acid

| | Used as a biomarker in: | |
| --- | --- | --- |
| Inflammation: | Blood | Urine |
| Cytokines | | |
| TNF-α (tumor necrosis factor α) | x | — |
| IL-6 (interleukin 6) | x | x |
| IL-8 (interleukin 8) | x | x |
| Several others | x | — |
| Other proteins | | |
| Osteopontin | x | x |
| Orosomucoid | — | x |
| Albumin | — | x |
| α1-microglobulin | — | x |
| Eicosanoids | | |
| PGE2 (prostaglandin E2) and metabolites | x | x |
| PGF2α (prostaglandin F2 α) and metabolites | x | x |
| Other molecules | | |
| Nitric oxide byproducts (NOx)(nitrate + nitrite) | x | x |
| Urinary proteins | no- | x |
| Histamine | x | x |

Figure 7:
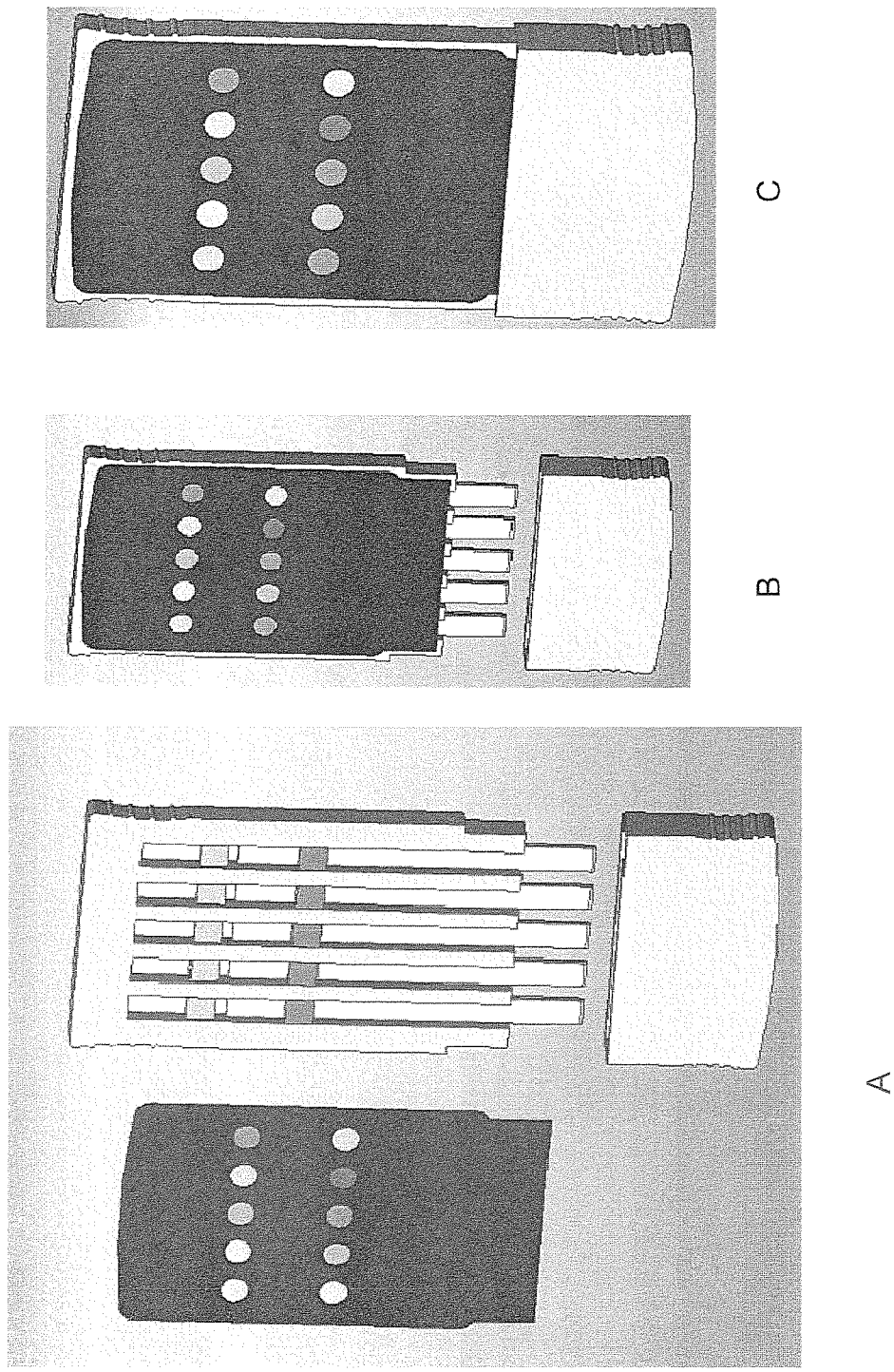
FIGS. 7A-7C are examples of a dry chemistry test panel in a dipstick format.
Figure 8:
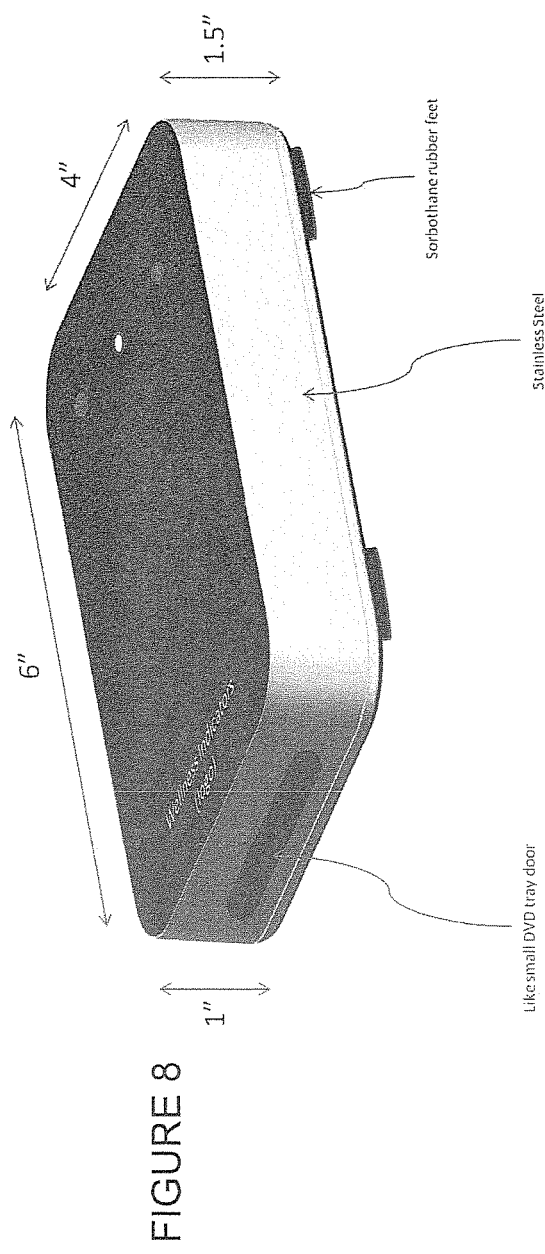
FIG. 8 is an example of a test panel.
Figure 9:
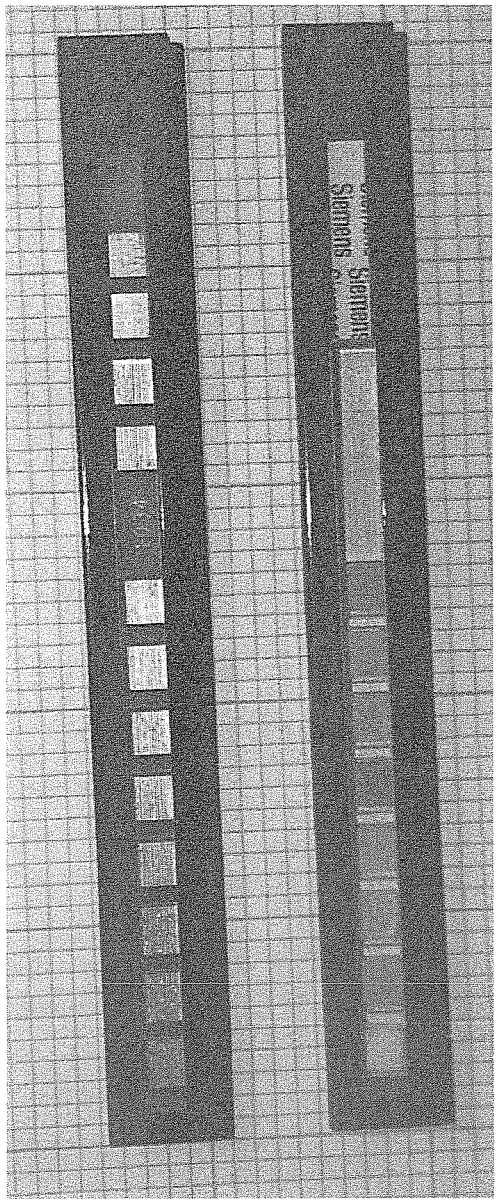
FIG. 9 is a photograph of an example of a test panel.

In a preferred embodiment, all of the biomarkers for an initial wellness screen are substances that can be quantified quickly by chemical or enzymatic reactions that do not require the use of antibodies, so that they can be incorporated into test panels that can be performed on simple chemical analyzers and/or incorporated into dry chemistry dipsticks that can be exposed to the specimen and subsequently quantified using a reflectance instrument similar to those that are widely available for other analytes. Alternatively, in other embodiments one or more of the biomarkers selected for inclusion in the panel can require the use of antibodies, including lateral flow immunoassays or immunoassays requiring the use of colorimetric, radiometric, fluorometric or chemiluminescent methods, or use more complicated analysis method(s) when collecting and/or quantifying samples in the liquid phase, such as microfluidic technologies, or microplate methods with automated or manual analysis in high throughput diagnostic machines. Examples of different test panels employing these methods are shown in FIGS. 7-9. It should be understood that while it is preferable for one method in a single device to be employed to detect and analyze the biomarkers in all three tests, each test can also use a different method. For example, one biomarker can be analyzed by immunoassay in a microplate, and another can be analyzed by a chemical indicator. When on a single device, preferably the tests are physically separate, such as having test pads on a hydrophobic backing dipstick material and blotting excess fluid for minimal crosstalk. However, having the tests on a single device can save time in obtaining results.

Whereas the analysis of oxidative stress, antioxidant and inflammatory biomarkers has previously been performed primarily using blood specimens, the preferred embodiment of the present invention employs urine specimens that can be obtained non-invasively by a less skilled individual and with less risk of exposure to blood-borne pathogens. Further, the levels of some of the biomarkers can be substantially altered for blood samples by release of constituents of red blood cells in hemolyzed specimens, or by the ex vivo oxidation of precursors (e.g. unsaturated lipids) upon exposure of blood to air. The panel of the present invention significantly reduces the generation of ex vivo artifacts and minimizes risks of alteration.

The panel of tests, preferably performed on urine specimens, provides a more robust assessment of an individual's health status than any of the individual components. More specifically, the panel includes at least tests for at least one biomarker each for inflammation, oxidative stress, and antioxidant activity, that are performed in the liquid phase (in test tubes or microplate wells), adapted to a simple dipstick method employing dried reagents as described above, or incorporated into a microfluidic or a lateral flow immunoassay device.

The oxidative stress test can include incorporating either a specific malondialdehyde (MDA) or 4-hydroxyonenal (4HNE) method to quantify lipid peroxidation and/or a thiobarbituric acid reactive substances (TBARS) method to measure a broader range of substances oxidized to aldehydes and ketones due to the actions of free radicals. These tests are known in the art and can be performed by an appropriate analyzing mechanism. Several other biomarkers can be used to test for oxidative stress and non-limiting examples are listed in Table 1 above. High levels of these biomarkers indicate that oxidative stress is occurring in an individual. Low levels of these biomarkers indicate a healthy individual. Examples of ranges are given in the FIGURES for both oxidative damage and oxidative stress calculated from oxidative damage and total antioxidant power.

Oxidative stress occurs when an abnormal level of reactive oxygen species (ROS), such as lipid peroxide, lead to damage of molecules in the body. ROS can be produced from fungal or viral infection, ageing, UV radiation, pollution, excessive alcohol consumption, and cigarette smoking among other diseases. ROS can further cause age-related macular degeneration and cataracts. The antioxidant power test, sometimes called the antioxidant capacity test, employs the CUPRAC (cupric reducing antioxidant capacity) method for measuring the sum of the antioxidant activity due to multiple species (uric acid, proteins, vitamins, dietary supplements) that are present in a urine sample (Özyürek, M., Güçlü, K. and Apak, R., The main and modified CUPRAC methods of antioxidant measurement. *Trends in Analytical Chemistry*, 30: 652-664 (2011)). Alternatively, or additionally, modified methods can be used to specifically measure or to discriminate among uric acid, ascorbic proteins or other substances that contribute to the overall antioxidant power, thereby monitoring what is referred to as the "antioxidant reserve." These tests are known in the art and can be performed by an appropriate analyzing mechanism. Several other biomarkers can be used to test for antioxidant power and non-limiting examples are listed in Table 1 above. Most of these tests require incubating the sample with a probe that changes on oxidation and then adding a radical generator. The longer it takes for the probe to change, the more antioxidant capacity there is. The CUPRAC method, and other methods that employ a redox indicator that directly measures the reaction of antioxidants with substances with appropriate redox potential to effect a color change. A higher value for antioxidant power, i.e. a greater amount of the biomarkers for antioxidant power, indicates a healthy individual because the individual has compounds that can neutralize free radicals that cause oxidative damage and stress. Examples of ranges of antioxidant power are shown in the FIGURES.

Inflammation is comprised of a complex series of physiological and pathological events, including the increased production of several proteins (e.g. cytokines such as IL-6 and IL-8, as well as COX-2 and the inducible form of nitric oxide synthase). The production of nitric oxide, by the inducible isoform of nitric oxide synthase can increase up to 1000 times during inflammation, and has been shown to be a useful biomarker for inflammation (Stichtenoth, D., Fauler, J., Zeidler, H., Frolich, J. C. Urinary nitrate excretion is increased in patients with rheumatoid arthritis and reduced by prednisolone Annals of the Rheumatic Diseases 54:820-824 (1995)). Because NO is relatively unstable, the production of NO can be tested by employing methods for the measurement of it degradation products nitrate and nitrite, i.e. measuring nitrite or the sum of nitrite and nitrate in a blood or urine sample, which are often abbreviated as NOx. These tests are known in the art and can be performed by an appropriate analyzing mechanism. Further, although very high levels of protein in urine are associated with kidney disease, it is known that the retention of blood proteins by the kidney is reduced by the effect of certain inflammatory cytokines, so that modest elevations in the levels of urinary proteins that are less than those associated with kidney disease can be used as a biomarker for inflammation. Several other biomarkers can be used to test for inflammation and non-limiting examples are listed in Table 1 above. Higher levels of inflammation biomarkers indicate that inflammation is occurring in an individual, possibly indicative of disease. Lower levels of inflammation biomarkers indicate a healthy individual. Examples of ranges of inflammation biomarkers are shown in the FIGURES. Chronic inflammation can lead to hay fever, atherosclerosis, and rheumatoid arthritis. Anti-inflammatory agents have also been shown to significantly reduce the incidence of heart disease, diabetes, Alzheimer's disease, and cancer.

The combination of the oxidative stress test, antioxidant power test, and inflammation test in this particular panel is unique. Pairs of these tests have been combined in the prior art. For example, Basu (Basu, S. Bioactive Eicosanoids: Role of Prostaglandin $F_{2\alpha}$ and $F_2$-Isoprostanes in Inflammation and Oxidative Stress Related Pathology. Mol. Cells 30: 383-391 (2010)) and others have monitored urinary biomarkers for oxidative stress and inflammation. Others have monitored antioxidant power and oxidative stress and computed an index for an individual's oxidative status (Vassalle C, Pratali L, Boni C, Mercuri A, Ndreu R. An oxidative stress score as a combined measure of the pro-oxidant and anti-oxidant counterparts in patients with coronary artery disease. Clin Biochem. 41:1162-7 (2008)). The use of biomarkers for oxidative stress (e.g. Isoprostanes like Basu uses) has been reported to be an independent risk factor for CVD. The use of antioxidant power and oxidative damage markers has been reported on frequently. Cutler, et al. (Ann. N.Y. Acad. Sci. 1055:136-158 (2005)) lists a large number of biomarkers for all three parameters and proposes that a large number of assays for this large number of biomarkers, employing both serum and urine (some technically very demanding, some not very reliable) to assess an individual but does not further provide guidance in the practical application and interpretation of this list of tests. However, while all three parameters of oxidative stress, antioxidant power, and inflammation have been mentioned together in the prior art, it has been within the context of a large listing of assays and not exclusively with regards to a practical method suitable for wide-spread application, in particular a non-invasive panel that can be performed using a set of tests on a urine specimen. Importantly, these research applications have not found their way into simple and widely useful testing methods.

Figure 4:
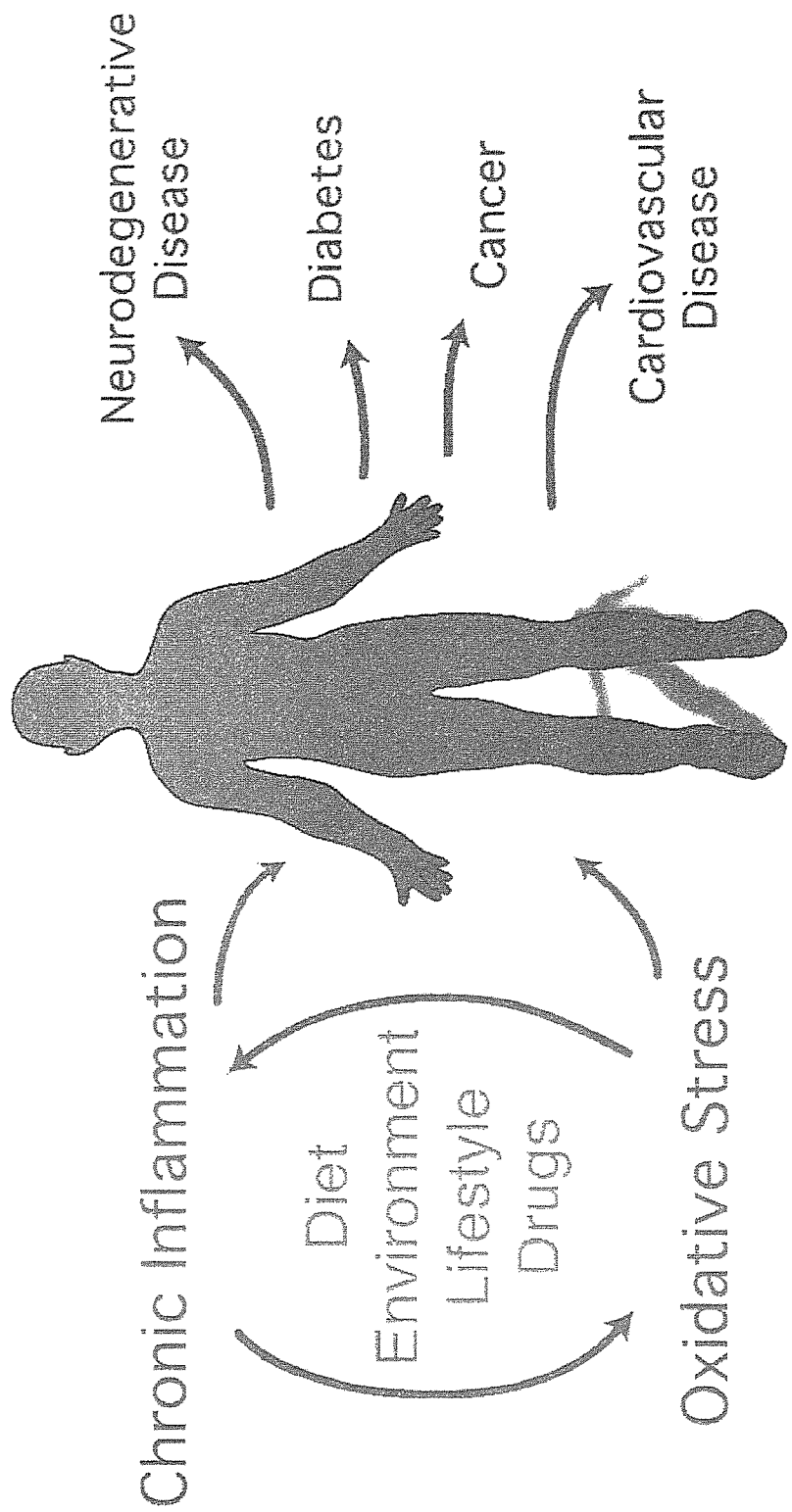
FIG. 4 is a diagram of an overview of how chronic inflammation and oxidative stress are interrelated.
Figure 5A:
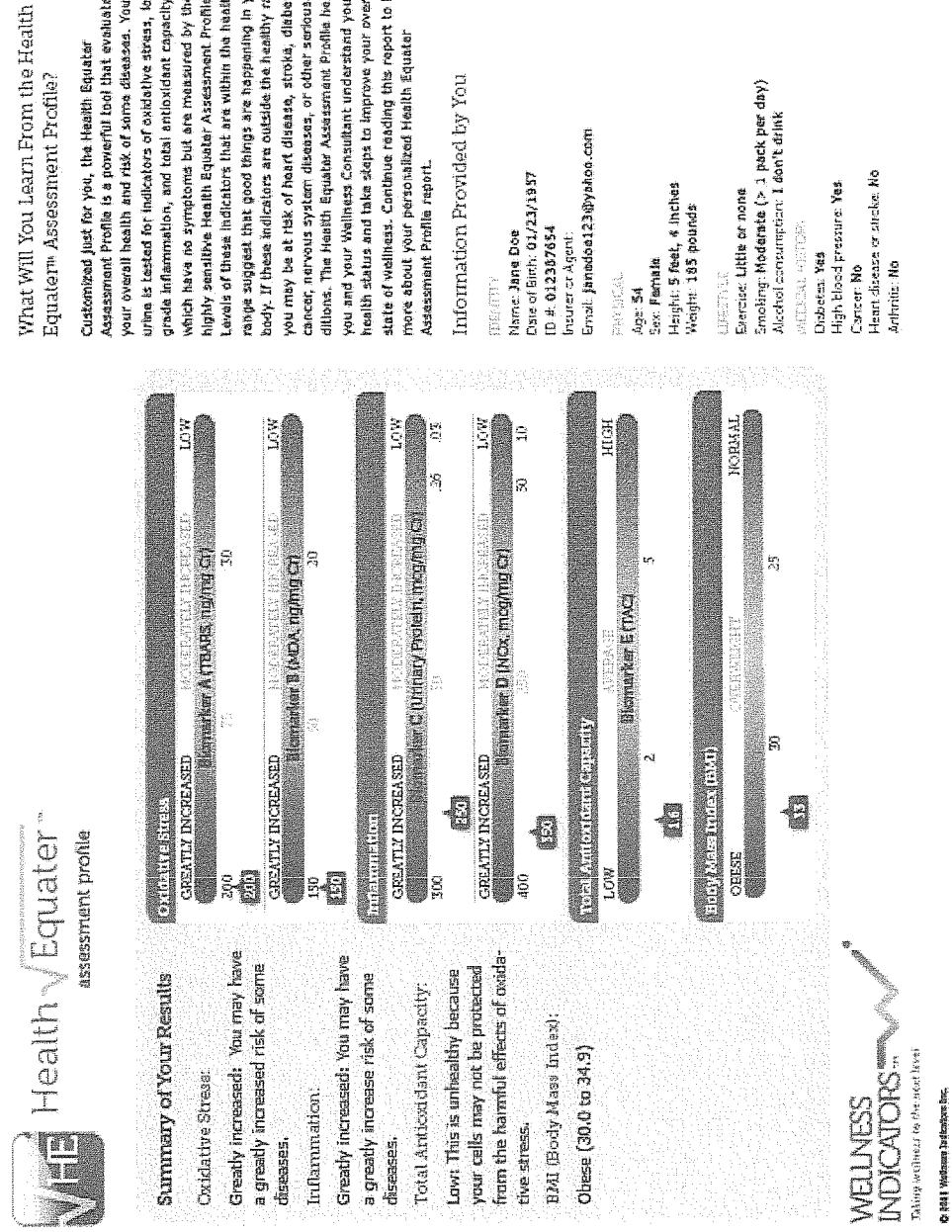
Figure 6A:
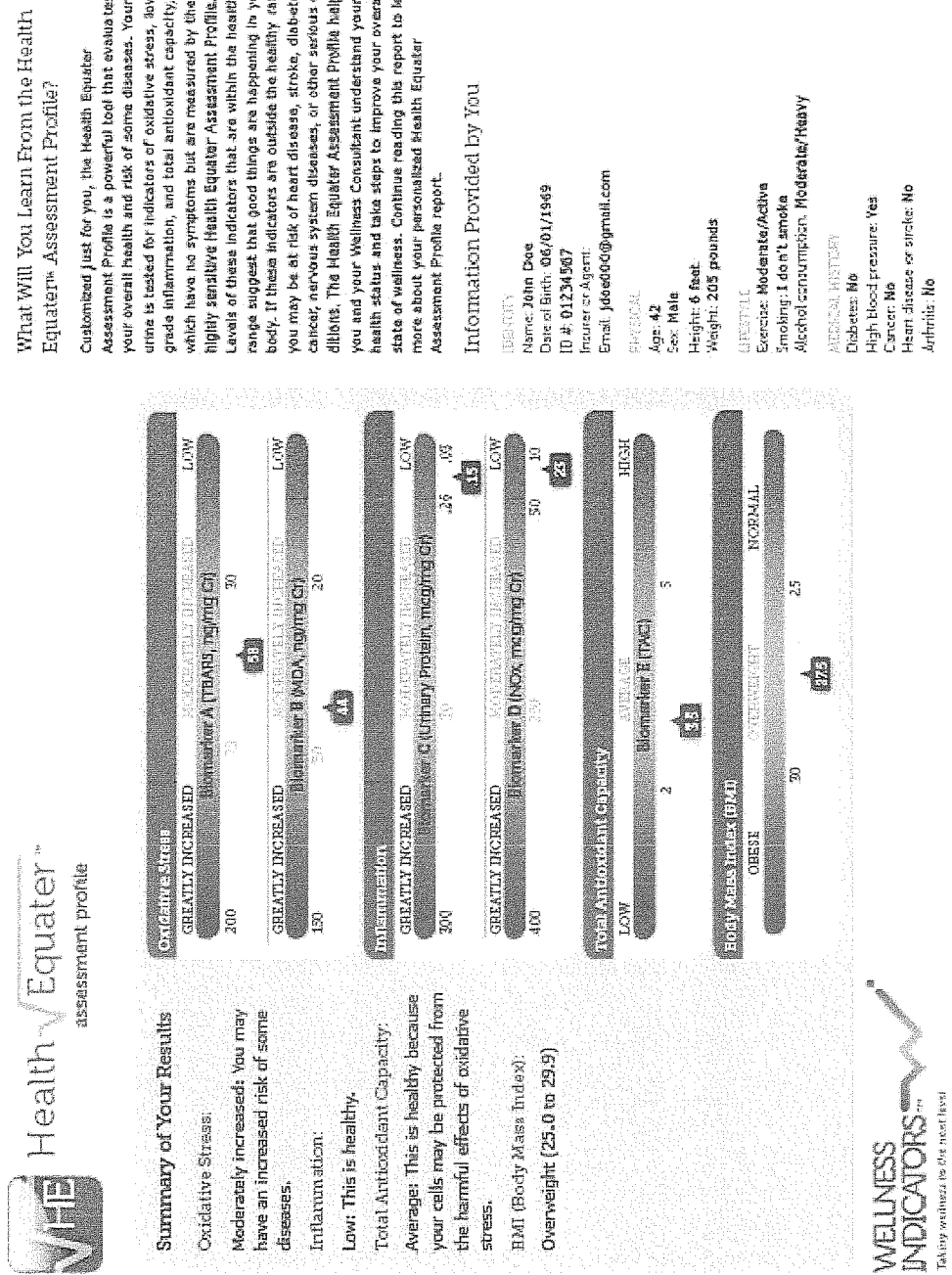

In the ten years since the sequencing of the human genome, it has become increasingly apparent that, while genetics plays a major role in the development of diseases for a small percentage of the population, the overall impact of genetics on major non-infectious diseases in humans is only about 15-20%. Much more important, especially for the development of the diseases that account for most morbidity and mortality in developed countries (chronic diseases such as cancer, cardiovascular diseases, neurodegenerative and autoimmune diseases) are the impact of diet, lifestyle (including exercise, smoking, alcohol use) and the environment. All of these factors influence an individual's health and, as illustrated in FIG. 4, they result in increases or decreases in inflammation and/or oxidative stress. Moreover, the oxidative stress can trigger some reactions that increase the level of inflammation.

The importance of oxidative stress to human health is evidenced by thousands of scientific publications and hundreds of biomarkers that have been reported for oxidative damage, as well as the development of several tests for antioxidant activity and the widespread application of one (the ORAC test) to measure the antioxidant activity in foods and juices, and the enormous market for nutraceutical supplements that have antioxidant activity in vitro. However, as has been now clearly demonstrated in the case of vitamin E, antioxidant activity in vitro does not necessarily translate into a change in the level of oxidative stress in vivo.

In keeping with traditional medical practices, some biomarkers for inflammation and oxidative damage have been translated individually into clinical practice. C-reactive protein is increasingly recognized inflammatory biomarker in blood (but not urine) that is used to monitor for development of cardiovascular disease. Levels of one specific protein, measured as the albumin/creatinine ratio, in urine is used clinically to measure microalbuminuria, with the increased levels of this specific protein associated with elevated risk for kidney and cardiovascular diseases. Similarly, elevated isoprostane levels (oxidative damage biomarkers in blood or urine) have been reported to be independent risk markers for cardiovascular disease with statistics comparable to CRP or HDL/LDL ratio, but isoprostane measurements are typically complex and have not found wide-spread application. However, the use of antioxidant power has been only applied to human biofluids in academic research studies, and the use of panels incorporating multiple biomarkers have been restricted to inflammatory biomarkers or oxidative stress biomarkers, typically without inclusion of antioxidant markers, and typically including inflammatory and oxidative stress markers only in very large, expensive, broad panels that include 20 or more biomarkers with comprehensive analysis or interpretation of the results referred to a physician.

The incorporation of a small number of relatively broad tests for oxidative damage and inflammation with a broad test for antioxidant activity provides, for the first time, a relatively rapid, broad, and affordable screening panel to assess an individual's wellness and susceptibility to major chronic diseases. By including information regarding their body mass index, and/or information regarding the test subject's age, lifestyle and disease history, and linking the numerical results to a database of specific interpretive narratives drawn from the scientific literature regarding the import of the data and methods (including specific diets, exercise, etc) to improve the values relative to a person's age, the panel provides an unprecedented approach to improved screening of broad populations for health and wellness, and for the feedback needed to help effect behavioral changes to improve health.

The panel can also include a normalization mechanism for urine concentration. The concentration of substances in urine can vary widely, depending on an individual's consumption of water, sweat, etc. Methods that allow for adjustment for urinary output include (a) performing studies on first morning specimens (most concentrated, but inconvenient, still variable and not always reliable), (b) collection of a 24-hour urine specimen (very reliable but very inconvenient and rarely used anymore), and (c) normalization of values to a metabolite that is excreted at a relatively constant rate or to the specific gravity of the specimen. Among the latter, creatinine is most commonly used. There are relatively few conditions for which the use of creatinine for normalization of the levels of substances in urine is not 100% accurate. Therefore, normalization of values to the concentration of creatinine is very common in clinical medicine, in medical research and there are several established methods for performing the assay. Therefore, all of the values related to oxidative stress, antioxidant power, and inflammation are divided by the creatinine concentration. This simple process significantly improves the reliability and reproducibility and permits the tracking of changes in an individual's wellness over time and as the result of changes in diet, lifestyle, etc.

Since it is also known that biological specimens, in particular urine, absorb light and that the color of a specimen is dependent on many endogenous substances as well as substances ingested in the diet or as medications, the panel can further include an adjustment mechanism for adjusting of the measurement for specific biomarker tests to eliminate to correct for color or fluorescence due irrelevant substances in the sample.

The panel can further include a data entry mechanism for entering an individuals age, height, and weight to calculate an individual's body mass index (BMI), as well as information regarding the individual's lifestyle (e.g. tobacco and/or alcohol use) and other factors. Since it is well documented that antioxidant activity declines with age and that oxidative stress tends to increase with age, age-related normalization can also be performed on the results. The BMI can be used in comparisons with the results of the three tests of the panel, i.e. BMI versus oxidative damage, BMI versus antioxidant power, BMI versus oxidative stress (OS) status, BMI versus inflammation, further described below. The BMI can be compared to the test results in order to determine risk for diseases.

The panel can also include a quantification device for analyzing test results as well as an output mechanism for displaying the results. These components and their use are further described below.

The panel of the present invention is used in the following method. The panel is used by collecting a sample from an individual (preferably urine), applying the sample to the panel, performing the tests for at least one biomarker for each of the three conditions described above, normalizing the values to correct for the relative concentration of the specimen and determining the levels of these biomarkers for health related to inflammation, oxidative stress, and antioxidant activity.

A sample for analysis by the panel is easily obtained from an individual's urine or other body fluid described above. The sample can be obtained by a cup to collect liquid for the microfluidic format or, most preferably, by a dipstick that is placed in the urine for the dipstick format. The urine can then be applied to the panel by inserting the dipstick therein.

The urine sample can optionally be treated with a substance that helps to preserve the components being measured from decomposition during storage or shipment, and/or prevents the generation of additional reactive substances outside of the body, and/or retards the growth of microbes in the specimen that might alter the values during storage or shipment. These additive(s) do not themselves alter the values of the tests involved in the panel. However, preferably, the sample is analyzed as soon as possible after collection to reduce the decomposition or further reactions of biomarkers in the panel.

Analysis of one or more biomarkers, preferably two each for oxidative stress and inflammation to improve reliability and reduce errors associated with confounding factors that can influence specific biomarkers, for each of the three conditions is performed as specified above by the panel. When a dipstick is used, detecting a color change in the dipstick can indicate the measurement of specific analytes or biomarkers in each test of the panel. Each test can change the amount of colored light reflected from one of the components of the dipstick. For a negative result (i.e. the presence of a biomarker is not detected), the strip can remain its original color, or it can change to a specific color. For a positive result (i.e. the presence of a biomarker is detected), the strip can change to a distinctively different color than the negative result. One example is the strip turning blue for a negative result and pink for a positive result. In preferred embodiments, the results are non-qualitative (color versus lack of color) but vary in degree corresponding to the level of the biomarker present. For example, an intense color can indicate the presence of high levels of the specified biomarker, and a muted color can indicate the presence of low levels of the biomarker.

Subsequently, the dipstick or other dry chemistry device can be inserted into an instrument that quantifies the reflected color for each test pad and a quantitative value can be recorded. In this method, the amount of each biomarker present can be determined to provide further information as to the health of the user. In other words, lower or higher levels of biomarkers, and not just their presence, can be relevant to the state of health. Alternatively, a quantification device is included in the panel itself and is not a separate device.

The quantification device can include or be coupled to a computer with software that is capable of performing analysis using the data thus obtained with an analyzing mechanism. The analyzing mechanism can compute values of each of the biomarkers in the tests, perform normalization as described above, as well as compute relationships of the test results with each other, the test results with BMI described above or, after calculating oxidative stress and antioxidant power, the ratio of both can be calculated to determine OS (oxidative stress) status and this value can be compared with BMI or inflammation. The analyzing mechanism can also search a database for facts relating high or low levels of specific biomarkers to disease risks, and can include facts derived from scientific literature that provide suggestions for lifestyle changes, or suggestions for further testing based on the test results, and combinations thereof.

Figure 2:
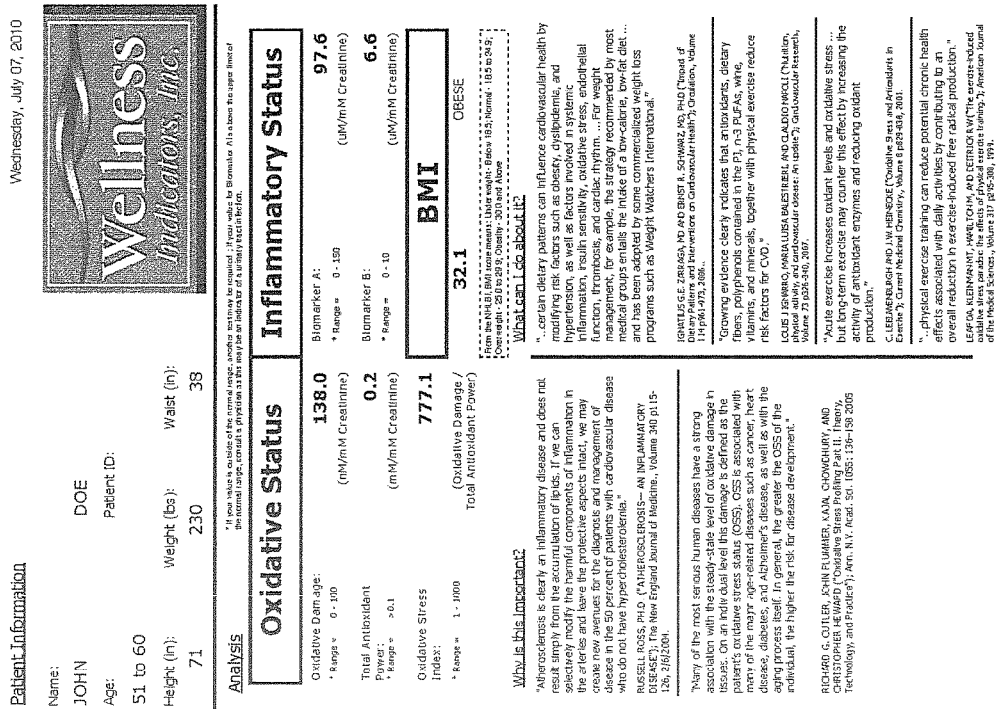
FIG. 2 is an example of a computer-generated report of the panel of the present invention for a healthy individual.
Figure 3:
FIG. 3 is an example of a computer-generated report of the panel of the present invention for an individual who smokes and has high OS and INF levels.

The presence of biomarkers for health can then be indicated to the user. The quantification device further includes an output mechanism to display the results in a meaningful way to an individual or health care practitioner. The display can be on a screen included on the panel and can include a printing mechanism for printing the results. Alternatively, the output mechanism can also send the results over wireless signals or wires to a PDA, smart phone, or a remote computer for print out or display. The results can be incorporated into a report on an individual's wellness that includes, but is not limited to, the results of the tests, comparison to the values and ratios computed to normal ranges that have previously been established for normal healthy men and women of different ages, ethnicities (if relevant) and/or other relevant parameters. Such a report can also incorporate historical data for an individual subject that was obtained using the same method(s). The report can further show the information from the database described above. Examples of such a report are shown in FIGS. 1-3 as well as in FIGS. 5A-5F and 6A-6F.

The panel of the present invention is useful for testing as part of wellness programs administered by insurance companies or large insurers, by employers, by clinicians, nutritionists, wellness consultants, and others as well as fitness and training programs administered by sports organizations or the military. The preferred use of the panel is a point of testing health and wellness assessment, which can be performed in a doctor's office, by a health care practitioner or an insurance agent after suitable training. The panel can also be used by individuals to monitor their health in their own home.

The panel of the present invention including the three tests provides better results than individual assays for the various biomarkers discussed herein. Tests for inflammation, oxidative stress, antioxidant activity have been studied independently and in controlled studies for large numbers of subjects, each has been associated with disease and/or disease risk. Oxidative stress and inflammation often increase or decrease together, and it is known that certain transcription factors are involved in this. e.g. oxidative stress turns on the expression of some genes encoding some inflammatory proteins and vice versa. However, each of the specific tests for oxidative stress and inflammation biomarkers is subject to some confounding factors as discussed above. Hence, elevated urinary protein can result from strenuous exercise or athletic training and not inflammation (although overexertion can cause inflammation); NOx may be falsely and transiently elevated by eating some hot dogs; MDA will transiently increase following athletic training— but endogenous sources for antioxidant activity are increased by exercise. By comparison to one's lipid profile, it is much more informative to measure a panel of biomarkers, just as one's cholesterol or HDL level alone does not provide as complete and accurate a picture. There are multiple endogenous and exogenous variable that can confound any of the assays in TABLE 1. By employing a panel with more than one but a manageable number of markers, one can improve the reliability of the overall panel versus one test or even one test for each condition.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A panel device system for measuring biomarker levels present in a urine sample taken from an individual comprising,
   a panel device comprising a plurality of assay tests,
   wherein each of the plurality of assay tests comprises a dry reagent test pad containing reagent specific for each one of the plurality of assay tests,
   wherein each of the plurality of assay tests is at a physically separate position on the panel device,
   wherein the plurality of assay tests comprises at least each of a test for measuring inflammation, oxidative stress, antioxidant activity, and urinary creatinine concentration;
   wherein the test for measuring inflammation comprises a measure of total nitric oxide metabolites, wherein the nitric oxide metabolites are nitrate and nitrite,
   wherein the test for oxidative stress measures malondialdehyde (MDA), and
   wherein the test for antioxidant activity measures cupric reducing antioxidant capacity (CUPRAC).

2. The panel device of claim 1, wherein the panel device further comprises at least one additional assay test for inflammation, wherein the at least one additional assay test comprises measuring at least one biomarker selected from the group consisting of tumor necrosis factor α (TNF-α), interleukin 6 (IL-6), interleukin 8 (IL-8), osteopontin, orosomucoid, albumin, α1-microglobulin, prostaglandin E2 (PGE2), prostaglandin F2 α (PGF2α), and histamine.

3. The panel device of claim 1, wherein the panel device further comprises at least one additional assay test for oxidative stress, wherein said one additional assay test measures at least one biomarker selected from the group consisting of a protein carbonyl, thiobarbituric acid reactive substance (TBARS), 4-hydroxynonenal, a lipid hydroperoxide, an isoprostane, a linoleic acid oxidation product, nitrotyrosine, a nitriothiol, 8-hydroxydeoxyguanosine, malondialdehyde deoxyguanosine (M1dG), an oxidized derivative of a ribose ring, selenium, glutathione (GSH), glutathione disulfide (GSSG), and GSH/GSSG ratio.

4. The panel device of claim 1, wherein the panel device further comprises at least one additional test for antioxidant activity, wherein the at least one additional test for antioxidant activity is selected from the group consisting of ferric reducing ability of plasma (FRAP), total reactive antioxidant potential (TRAP), oxygen radical absorbance capacity (ORAC), and hydroxyl radical antioxidant capacity (HORAC).

5. The panel device system of claim 1, wherein each of the plurality of assay tests of the panel device results in a color change when the result is a positive result.

6. The panel device system of claim 5, further comprising an instrument for receiving the panel device, wherein the instrument quantifies said color change for each of said plurality of assay tests when said panel device is inserted therein.

7. The panel device system of claim 6, wherein said instrument further displays and exports the quantified color changes to a computer and produces printed reports.

8. The panel device system of claim 7, wherein said computer normalizes measured biomarker levels to the result of the measured creatinine concentration.

9. A method for monitoring inflammation, oxidative stress and antioxidant activity of an individual, the method comprising:
   (a) collecting a sample from the individual;
   (b) applying the sample to the panel device of claim 1;
   (c) obtaining a result for each of, the test for inflammation, the test for oxidative stress, and the test of antioxidant activity from the panel device of claim 1.

10. The method of claim 9, wherein said collecting step comprises collecting a sample that is urine.

11. The method of claim 9, wherein said collecting step further comprises an additional step selected from the group consisting of preserving the sample from decomposition, preventing generation of additional reactive substances, retarding growth of microbes in the sample, and combinations thereof.

* * * * *